United States Patent
Nakayama et al.

(10) Patent No.: US 9,956,074 B2
(45) Date of Patent: May 1, 2018

(54) VALVED STENT, BASE MATERIAL FOR FORMING VALVED STENT, AND METHOD FOR PRODUCING VALVED STENT

(71) Applicants: SHINIKAN KOGYO K.K., Osaka (JP); National Cerebral and Cardiovascular Center, Osaka (JP)

(72) Inventors: Yasuhide Nakayama, Osaka (JP); Tomonori Oie, Osaka (JP)

(73) Assignees: SHINKAN KOGYO K.K., Osaka (JP); NATIONAL CEREBRAL AND CARDIOVASCULAR CENTER, Osaka (JP)

(*) Notice: Subject to any disclaimer, the term of this patent is extended or adjusted under 35 U.S.C. 154(b) by 191 days.

(21) Appl. No.: 14/591,379

(22) Filed: Jan. 7, 2015

(65) Prior Publication Data
US 2015/0119970 A1    Apr. 30, 2015

Related U.S. Application Data

(62) Division of application No. 13/822,765, filed as application No. PCT/JP2012/072980 on Sep. 7, 2012, now abandoned.

(30) Foreign Application Priority Data

Sep. 9, 2011    (JP) ................. 2011-197663

(51) Int. Cl.
*A61F 2/24* (2006.01)
*B32B 1/00* (2006.01)
(Continued)

(52) U.S. Cl.
CPC .......... *A61F 2/2415* (2013.01); *A61F 2/2412* (2013.01); *A61F 2/2418* (2013.01);
(Continued)

(58) Field of Classification Search
CPC .... A61F 2/2412; A61F 2/2415; A61F 2/2418; A61F 2/2475; A61F 2240/004; A61F 2002/072
See application file for complete search history.

(56) References Cited

U.S. PATENT DOCUMENTS 6,666,886 B1    12/2003  Tranquillo et al.
2003/0027332 A1  2/2003  Lafrance et al.
(Continued)

FOREIGN PATENT DOCUMENTS

JP    2005-500101    1/2005
JP    2007-37763     2/2007
(Continued)

OTHER PUBLICATIONS

European Search Report dated Mar. 13, 2015 issued in corresponding European Patent Application No. 12826657.4.
(Continued)

*Primary Examiner* — Howie Matthews
(74) *Attorney, Agent, or Firm* — Wenderworth, Lind & Ponack, L.L.P.

(57) ABSTRACT

The present invention provides a valved stent that can provide a valve function without blocking a branch blood vessel, and also can provide a valve function with minimum covering of blood vessel tissue in a stent indwelling section. Specifically, a cylindrical stent body 4 is provided. A leaflet 5 that can open/close a blood vessel 2 in a blood flow direction is provided. The leaflet 5 is composed of connective tissue and protrudes radially inward from the stent body 4. An inside and an outside of the stent body 4 radially communicate with each other. The stent does not block a branch blood vessel 8. An area of the blood vessel covered with the stent is reduced.

3 Claims, 31 Drawing Sheets

(51) Int. Cl.
   *A61F 2/82* (2013.01)
   *A61F 2/07* (2013.01)
   *A61F 2/06* (2013.01)

(52) U.S. Cl.
   CPC .................. *B32B 1/00* (2013.01); *A61F 2/07* (2013.01); *A61F 2/2475* (2013.01); *A61F 2/82* (2013.01); *A61F 2002/061* (2013.01); *A61F 2002/072* (2013.01); *A61F 2230/0054* (2013.01); *A61F 2240/001* (2013.01); *A61F 2240/004* (2013.01); *Y10T 428/2933* (2015.01)

(56) References Cited

U.S. PATENT DOCUMENTS

| | | |
|---|---|---|
| 2006/0149360 A1 | 7/2006 | Schwammenthal et al. |
| 2006/0259136 A1 | 11/2006 | Nguyen et al. |
| 2007/0154515 A1 | 7/2007 | Johnson et al. |
| 2007/0213813 A1 | 9/2007 | Von Segesser et al. |
| 2010/0082094 A1 | 4/2010 | Quadri et al. |
| 2010/0168839 A1 | 7/2010 | Braido et al. |

FOREIGN PATENT DOCUMENTS

| | | |
|---|---|---|
| JP | 2007-37764 | 2/2007 |
| JP | 2007-312821 | 12/2007 |
| JP | 2008-237896 | 10/2008 |
| JP | 2008-537891 | 10/2008 |
| JP | 2009-520535 | 5/2009 |
| JP | 2010-088625 | 4/2010 |
| JP | 2010-94476 | 4/2010 |
| JP | 2011-25002 | 2/2011 |
| WO | 2010/037141 | 4/2010 |

OTHER PUBLICATIONS

International Search Report dated Dec. 4, 2012 in International (PCT) Application No. PCT/JP2012/072980.
European Search Report dated Jul. 30, 2015 issued in corresponding European Patent Application No. 12826657.4.
Yasuhide Nakayama, Ph.D., et al., "Development of in vivo tissue-engineered autologous tissue-covered stents (biocovered stents)," Journal of Artificial Organs; The Japanese Society for Artificial Organs, (2007); vol. 10, pp. 171-176.

VALVED STENT, BASE MATERIAL FOR FORMING VALVED STENT, AND METHOD FOR PRODUCING VALVED STENT

TECHNICAL FIELD

The present invention relates to a valved stent indwelled in a blood vessel to provide a valve function to the blood vessel, a base material for forming the valved stent, and a method for producing the valved stent.

BACKGROUND ART

Many studies have been made on regenerative medicine for regenerating cells, tissue, or organs damaged by diseases or accidents with artificial materials or cells. Normally, it is known that a body has a self-protective function, and when foreign matter such as a thorn enters a shallow position in the body, the body tries to force the foreign matter out of the body, while when foreign matter enters a deep position in the body, fibroblasts aggregate around the foreign matter, and a capsule of connective tissue mainly composed of fibroblasts and collagen is formed to cover the foreign matter, thereby isolating the foreign matter in the body. A plurality of methods are reported in which using the latter self-protective reaction, tubular tissue derived from a living body with living cells in a living body is formed (see Patent Literatures 1 to 3).

Patent Literature 4 discloses a stent in which, for example, a mesh-like tubular biocompatible stent body of metal is entirely covered with a connective tissue layer, and an artificial valve is formed integrally with the connective tissue layer. The stent is covered with a connective tissue film formed in a living body, and the tissue film is rich in matrix such as collagen, thereby allowing vascular endothelium to be rapidly organized and reconstructed.

CITATION LIST

Patent Literature

Patent Literature 1: Japanese Patent Laid-Open No. 2007-312821
Patent Literature 2: Japanese Patent Laid-Open No. 2008-237896
Patent Literature 3: Japanese Patent Laid-Open No. 2010-094476
Patent Literature 4: Japanese Patent Laid-Open No. 2007-037763 (claim 1, paragraphs 0029, 0037 to 0039)

SUMMARY OF INVENTION

Technical Problem

Some blood vessels such as an aortic sinus (sinus of Valsalva) of an aorta include an ampulla with a blood vessel wall expanding radially outward, and a plurality of leaflets that protrude radially inward are opened/closed in a blood flow direction inside and on an upstream side of the ampulla. The ampulla functions as an escape path for blood when a valve is opened, and functions as a reservoir for the blood when the valve is closed, thereby facilitating opening/closing of the valve and preventing backflow of the blood.

There is a need for an artificial valve provided in such an ampulla of the blood vessel, and it is considered that the stent in Patent Literature 4 is indwelled in the ampulla to provide a valve function.

However, a coronary artery having an influence on a heart branches off from an aortic sinus of an aorta, and when the stent in Patent Literature 4 is indwelled in the aortic sinus as an aortic valve, the connective tissue layer covering the entire stent may block the coronary artery to cause myocardial infarction.

On the other hand, the stent in Patent Literature 4 is covered with a connective tissue film, and thus the vascular endothelium can be rapidly organized and reconstructed. However, in some cases, the connective tissue film covering the stent body may cover blood vessel tissue in a stent indwelling section to increase risk of a blood clot in a blood vessel and retard healing.

The present invention has an object to provide a valved stent that can provide a valve function without blocking a branching blood vessel and that can also provide a valve function with minimum covering of blood vessel tissue in a stent indwelling section, a base material for forming the valved stent, and a method for producing the valved stent.

Solution to Problem

To achieve the object, the present invention provides a valved stent indwelled in a blood vessel to provide a valve function to the blood vessel, including: a cylindrical stent body; and a leaflet composed of connective tissue that protrudes radially inward from the stent body and is capable of opening/closing the blood vessel in a blood flow direction, wherein an inside and an outside of the stent body radially communicate with each other.

According to the above described configuration, the inside and the outside of the stent body radially communicate with each other, and thus even if the stent is indwelled in an aortic sinus of an aorta or the like from which a coronary artery branches off, an artificial valve as an aortic valve can be provided to provide a valve function without blocking the branch blood vessel by the stent, for example. Also, because the inside and the outside of the stent body radially communicate with each other, an area of the blood vessel covered with the stent can be minimized to leave the blood vessel tissue in the stent indwelling section substantially intact. This allows an artificial valve to be provided in an aorta or a pulmonary artery, and also reduces risk of a blood clot and facilitates healing.

As the stent body, a mesh-like metal member can be exemplified. This configuration can provide sufficient strength of the stent, also minimize an area where communication between the inside and the outside of the stent body is prevented, and further easily increases a diameter of the stent body to a desired diameter. The stent body may be any member such as a synthetic resin cylinder having a communication hole, and is not limited to the mesh-like metal member, as long as the inside and the outside of the stent body communicate with each other.

The stent may be indwelled in an ampulla with a blood vessel wall of the blood vessel expanding radially outward, and the stent body may be set to a length such that the stent body can span the ampulla in a blood flow direction and be held on opposite sides. According to this configuration, the stent can span the ampulla of the blood vessel and be held on the opposite sides, thereby allowing a linear stent to be indwelled in the ampulla with a gap between the blood vessel wall of the ampulla and the stent. When the artificial valve is closed, the blood in the stent once flows through a wide range of the cylindrical wall of the stent into the gap between the blood vessel wall of the ampulla and the stent, and flows from the gap to the branch blood vessel, thereby allowing the blood to be smoothly fed to the branch blood vessel.

A plurality of leaflets may be arranged in parallel in a circumferential direction of the stent body, and the plurality of leaflets may be integrated at its base end. According to this configuration, the plurality of leaflets are arranged in the circumferential direction, and also the leaflets are integrated at the base end to constitute an artificial valve. This provides substantially the same configuration as an aortic valve or a pulmonary valve constituted by a trileaflet valve.

A contact section that covers the stent body and that comes into contact with the blood vessel wall may be composed of connective tissue, and a plurality of the contact sections may be continuously formed in the blood flow direction at intervals in the circumferential direction of the stent body to expose the stent body between the plurality of contact sections.

According to this configuration, the contact section is formed of the connective tissue, thereby preventing the stent body from coming into direct contact with the blood vessel wall as foreign matter. Also, the stent body is exposed between the plurality of contact sections, thereby providing communication between the inside and the outside of the stent body at the respective exposed portions of the stent body. A structure in which a leaflet is simply provided in the stent body may be used without the contact section being formed of the connective tissue. In this case, for example, the stent body may be made of biocompatible metal such as stainless, titanium, tantalum, aluminum, tungsten, nickel-titanium alloy, cobalt chrome alloy, or titanium-aluminum-vanadium alloy; biodegradable magnesium alloy; or hydrolyzable polymer such as polylactic acid.

The contact section may be formed so as to be aligned with a boundary between the plurality of leaflets in the circumferential direction of the stent body. According to this configuration, the opposite ends of the leaflet can be continuous with the contact sections, and the leaflet can be firmly integrated with the stent body in three positions at the base end and the opposite sides. Further, the exposed section that provides communication between the inside and the outside of the stent can be circumferentially aligned with the leaflet. This provides substantially the same configuration as the aortic valve or the pulmonary valve in which the leaflet is circumferentially aligned with the branch blood vessel.

The present invention also provides a base material for forming a valved stent that is placed in an environment with a body tissue material to form film-like tissue on a surface of the base material and form a valved stent including a leaflet protruding radially inward from a stent body, including: a columnar base material body; a plurality of recesses formed in an outer peripheral surface of the base material body; an inner cover that covers the recesses to form a leaflet forming space for forming the leaflet; and an outer cover placed on an outer surface side of the inner cover with the stent body interposed therebetween.

According to the above-described configuration, the recesses in the base material body are covered with the inner cover to form the leaflet forming space. Thus, when the film-like tissue is formed on the surface of the base material, the tissue may enter the leaflet forming space to form the leaflet, and also each leaflet forming section forms each leaflet, thereby eliminating the need to cut the leaflet. Further, the outer cover is placed on the outer surface side of the inner cover with the stent body interposed therebetween. This prevents the tissue from being formed in a region of the stent body between the inner cover and the outer cover, and can form an exposed portion that provides communication between the inside and the outside of the stent body, and the inner cover can also serve as a member for forming the leaflet and the exposed portion. The leaflet may be integrated with the stent body in a region where the tissue enters the leaflet forming space.

In the present invention, the "body tissue material" is a material required for forming desired tissue derived from a living body, and includes, for example, animal cells such as fibroblasts, smooth muscle cells, endothelial cells, stem cells, ES cells, or iPS cells, various proteins (collagen or elastin), saccharides such as hyaluronic acid, and other cells, cell growth factors, or various physiologically active substances in the living body such as cytokine. The "body tissue material" includes materials derived from mammals such as humans, dogs, cows, pigs, goats or sheep, or from birds, fish, and other animals, and artificial materials comparable thereto.

Also, "in the environment with a body tissue material" refers to an inside of a living body (for example, embedding under skin of four limbs, lumber, back, or abdomen, or into abdominal cavity) of animals (mammals such humans, dogs, cows, pigs, goats or sheep, or birds, fish, and other animals) or to an artificial environment containing a body tissue material outside a living body of animals. Embedding into animals is preferably performed by a less invasive method with a minimum incision under sufficient anesthesia in a spirit of animal protection.

The inner cover and the outer cover preferably have open sections that expose a boundary between the plurality of recesses in the outer peripheral surface of the base material body via the stent body. According to this configuration, the inner cover and the outer cover have the open sections. Thus, tissue that covers the stent body is formed on a surface of the boundary between the recesses in the base material body to be a contact section that comes into contact with the blood vessel wall, the opposite sides of the leaflet can be continuous with the contact section, and the leaflet can be firmly integrated with the stent body in three positions at the base end and the opposite sides. Further, the recesses in the base material body are covered with the inner cover and the outer cover, and thus the inner cover and the outer cover can hold the stent body therebetween to form the exposed portion, and the exposed portion of the stent body is circumferentially aligned with the leaflet to provide substantially the same configuration as the aortic valve and the pulmonary valve.

A positioning section that circumferentially positions the base material body, the inner cover, and the outer cover is preferably provided. According to this configuration, the base material body, the inner cover, and the outer cover can be positioned, thereby preventing misalignment thereof, and ensuring formation of the leaflet and the exposed portion of the stent body.

The present invention provides a method for producing a valved stent including: an assembly step of assembling a base material for forming the valved stent described above by incorporating a stent body between an inner cover and an outer cover; a placement step of placing the base material for forming the valved stent in an environment with a body tissue material; a formation step of forming film-like tissue around the base material for forming the valved stent; a taking-out step of taking out the base material for forming the valved stent covered with tissue from the environment; and a separation step of integrally delaminating and taking out tissue including the leaflet and the stent body from the base material for forming the valved stent as a valved stent, wherein the separation step is a step of removing tissue on surfaces of opposite ends of the base material for forming the valved stent and the outer cover, detaching the outer cover, and then central-axially disassembling and taking out the base material body and the inner cover from a lumen of the valved stent. In the present invention, for the transplant recipient, any of autologous transplantation, allotransplantation, and heterotransplantation may be performed, but autologous transplantation or allotransplantation is preferable in order to prevent rejection. For the heterotransplantation, elimination of immunogen such as known decellularization is preferably performed in order to avoid rejection.

The present invention provides a base material for forming a valved stent that is placed in an environment with a body tissue material to form film-like tissue on a surface of the base material and form a reverse valved stent with an inside and an outside being reversed of a valved stent including a leaflet protruding radially inward from a stent body, including: a columnar base material body; and a base material cover placed on an outer peripheral side of the base material body with the stent body interposed therebetween.

According to the above-described configuration, the base material cover is placed on the outer peripheral side of the base material body with the stent body interposed therebetween. Thus, the film-like tissue is formed on the surface of the base material, and the leaflet can be formed on the outer surface of the base material cover outside the stent body. Thus, the reverse valved stent having the leaflet on the outer peripheral side of the stent body can be formed without covering the stent body with tissue, and the reverse valved stent can be reversed to obtain a valved stent.

Further, when the reverse valved stent is formed, the leaflet is formed on the outer surface of the base material cover placed on the outer peripheral side. This eliminates the need to form the leaflet by causing the tissue to enter deep into a narrow space, and allows a thin leaflet to be reliably formed in a short time. The leaflet may be integrated with the stent body via tissue formed in a region where the base material body is exposed from the base material cover, or tissue slightly entering a gap between the base material cover and the base material body.

The base material cover preferably has an open section that exposes the outer peripheral surface of the base material body via the stent body. According to this configuration, the base material cover has the open section, and thus tissue covering a part of the stent body can be formed on the surface of the base material body, and the leaflet and the stent body can be integrated via the tissue.

Further, the outer peripheral surface of the base material body may have an entry groove that connective tissue enters, and the base material cover may be placed so that the entry groove is aligned with the open section. According to this configuration, the tissue enters the entry groove to cover a part of the stent body from the inside and the outside. Thus, the leaflet and the stent body can be more firmly integrated via the tissue.

The base material cover may have a bulge formed by expanding an outer surface side. According to this configuration, the leaflet can be expanded to an enough size to more reliably prevent backflow of blood or the like. Further, the base material cover has the bulge, and thus thin tissue with a sufficient modulus of elasticity can be formed on the surface of the base material cover.

The present invention provides a method for producing a valved stent including: an assembly step of assembling a base material for forming the valved stent described above by incorporating a stent body between a base material body and a base material cover; a placement step of placing the base material for forming the valved stent in an environment with a body tissue material; a formation step of forming film-like tissue around the base material for forming the valved stent; a taking-out step of taking out the base material for forming the valved stent covered with tissue from the environment; and a separation step of integrally delaminating and taking out tissue including the leaflet and the stent body from the base material for forming the valved stent as a reverse valved stent, wherein the separation step is a step of removing tissue on opposite ends of the base material for forming the valved stent, then central-axially disassembling the base material body and the base material cover, taking out the base material cover from between the leaflet and the stent body, and taking out the base material body from a lumen of the reverse valved stent, and the method further includes, after the separation step, a reverse step of reversing an inside and an outside of the reverse valved stent to form a valved stent.

Advantageous Effects of Invention

As described above, according to the present invention, the inside and the outside of the stent body radially communicate with each other, thereby providing a valve function to an aortic sinus or the like without blocking a branch blood vessel such as a coronary artery. Further, the communication of the stent body can minimize an area of the blood vessel covered with the stent to leave the blood vessel tissue in the stent indwelling section substantially intact. This provides a valve function to an aorta or a pulmonary artery, and also reduces risk of a blood clot and facilitates healing.

DESCRIPTION OF EMBODIMENTS

Figure 1:
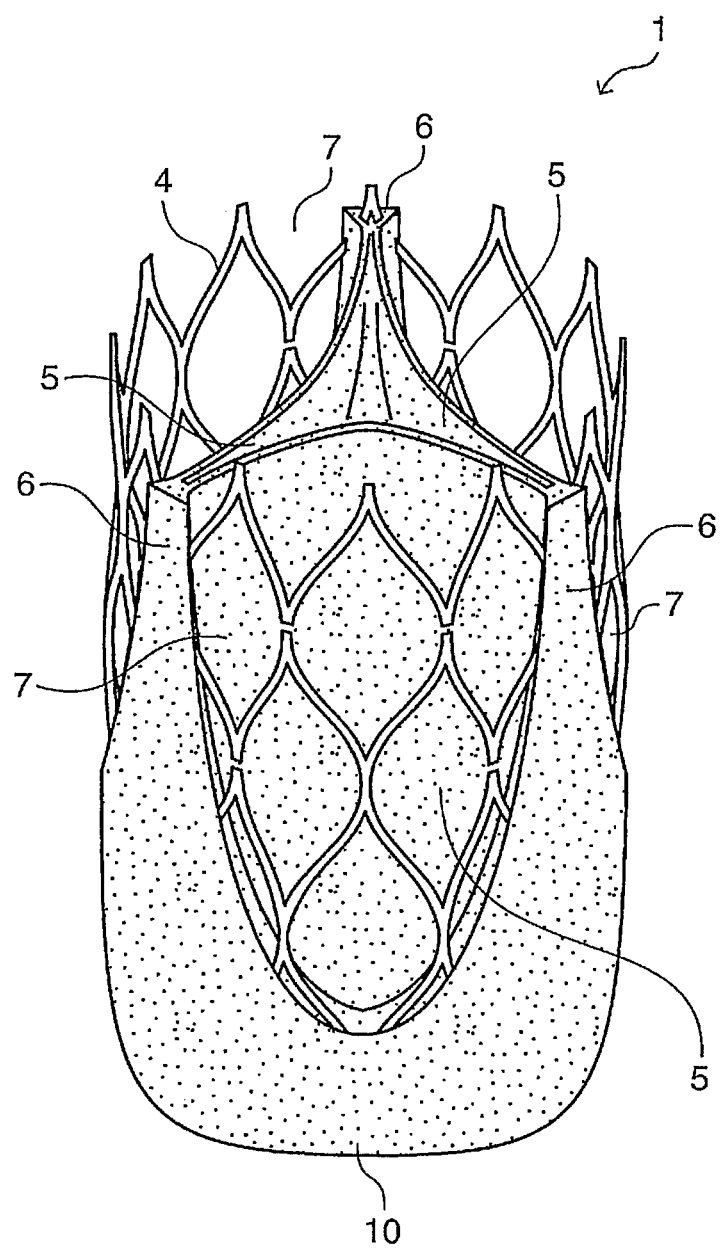
FIG. 1 is a perspective view of a valved stent according to the present invention.

Now, first to fifth embodiments of a valved stent, a base material for forming a valved stent, and a method for producing the valved stent according to the present invention will be described with reference to the drawings.

First Embodiment

As shown in FIGS. 1 to 8, a valved stent 1 is, for example, indwelled in an ampulla 3 of a blood vessel 2 having a blood vessel wall expanding radially outward, such as an aortic sinus of an aorta, to provide a valve function to the blood vessel 2, and includes a cylindrical stent body 4, a leaflet 5 composed of connective tissue that protrudes radially inward from the stent body 4 and is capable of opening/closing the blood vessel 2 in a blood flow direction, and a contact section 6 composed of connective tissue that covers the stent body 4 and comes into contact with the blood vessel wall.

The stent body 4 is a mesh-like metal member, for example, with thin metal wires arranged in a diagonal grid pattern, an inside and an outside of the stent body 4 radially communicating with each other at an exposed portion 7 between a plurality of such contact sections 6, and is set to a length such that the stent body 4 can span the ampulla 3 in the blood flow direction and be held on opposite sides. The stent body 4 is preferably made of biocompatible metal such as stainless, titanium, tantalum, aluminum, tungsten, nickel-titanium alloy, cobalt chrome alloy, titanium-aluminum-vanadium alloy; biodegradable magnesium alloy; or hydrolyzable polymer such as polylactic acid.

Figure 6:
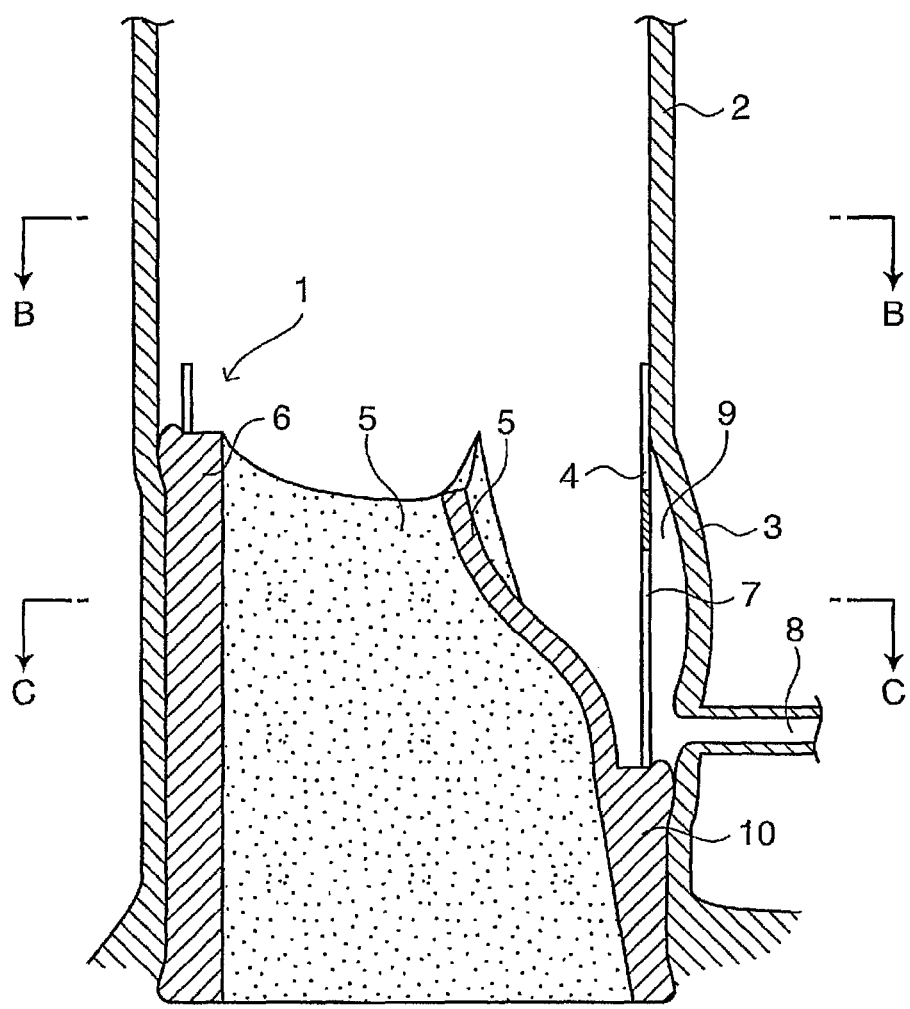
FIG. 6 is a vertical sectional view of the valved stent indwelled in an ampulla of a blood vessel.
Figure 7:
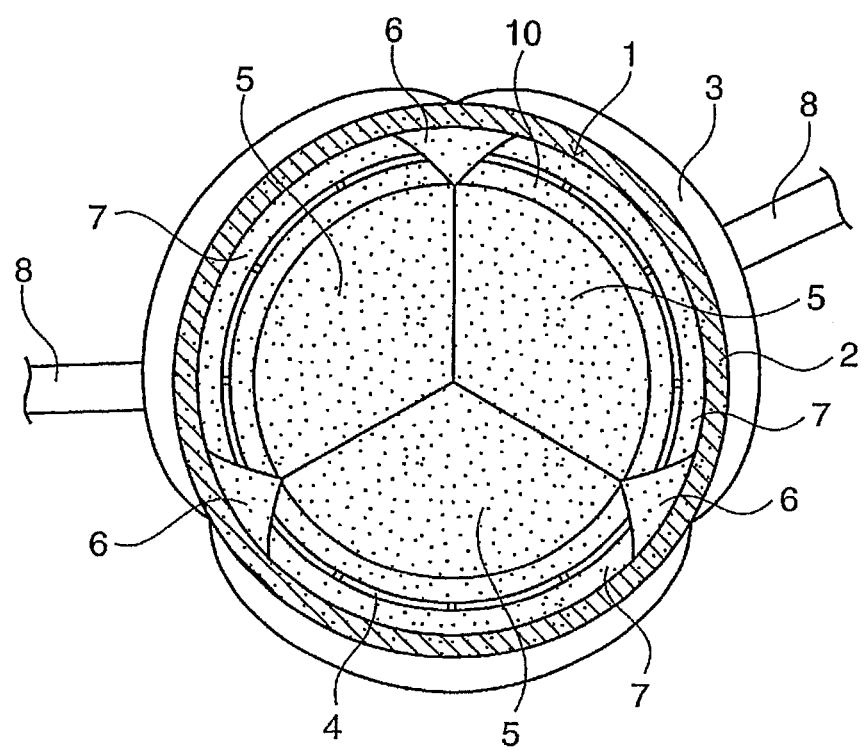
FIG. 7 is a B-B sectional view of FIG. 6.
Figure 8:
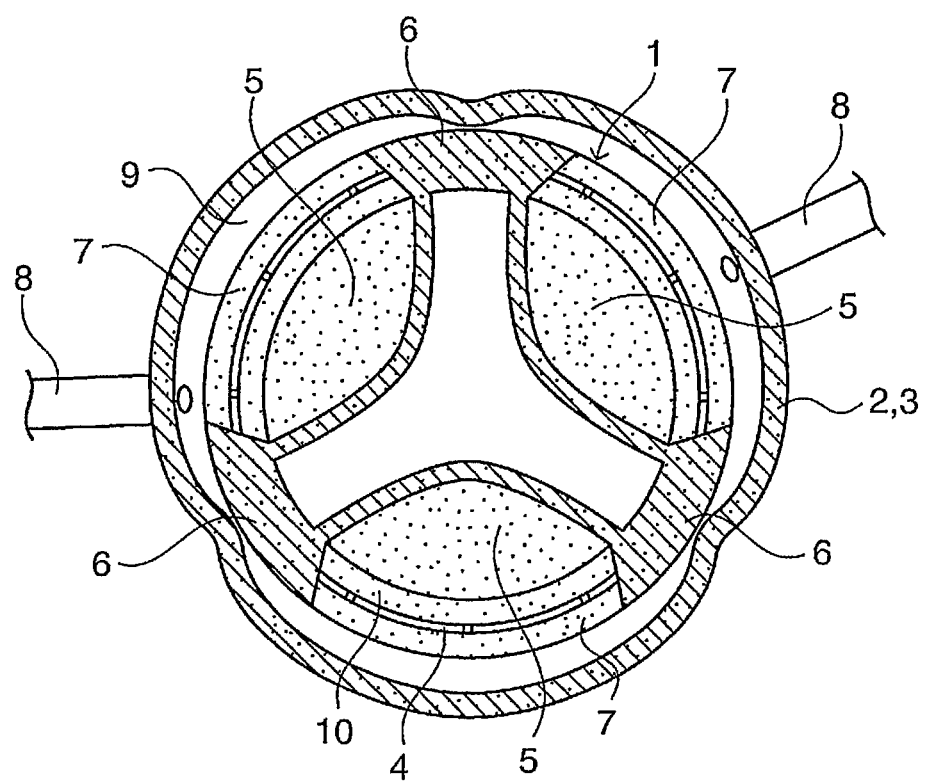
FIG. 8 is a C-C sectional view of FIG. 6.
Figure 9:
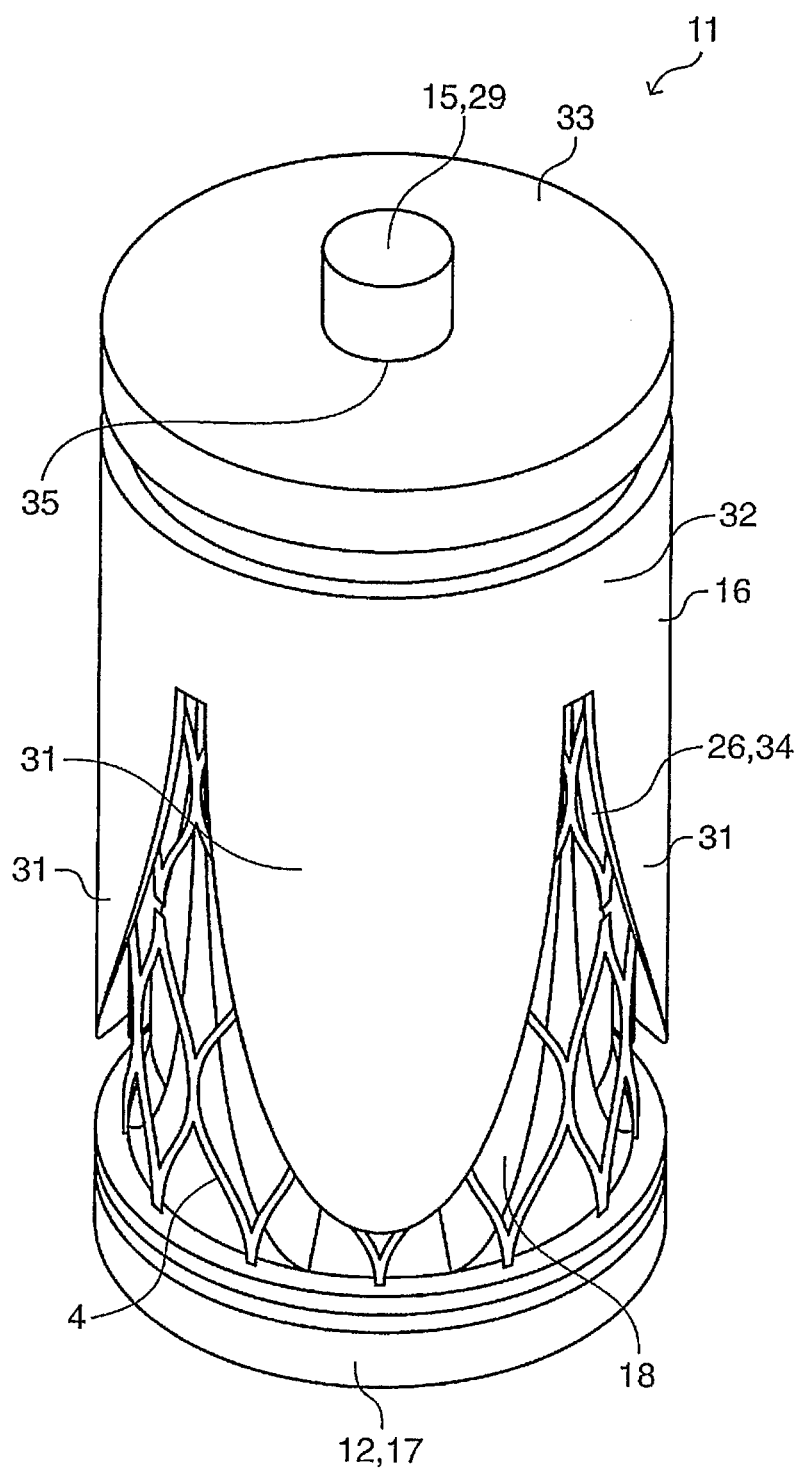
FIG. 9 is a perspective view of a base material for forming a valved stent (first embodiment).
Figure 10:
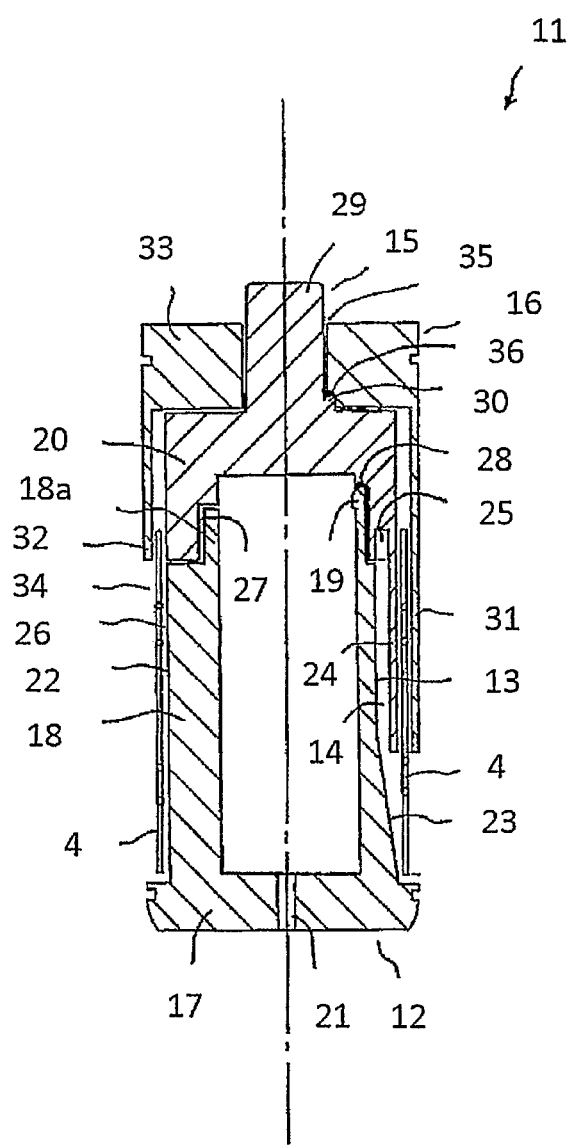
FIG. 10 is a vertical sectional view of the base material for forming a valved stent (first embodiment).
Figure 11:
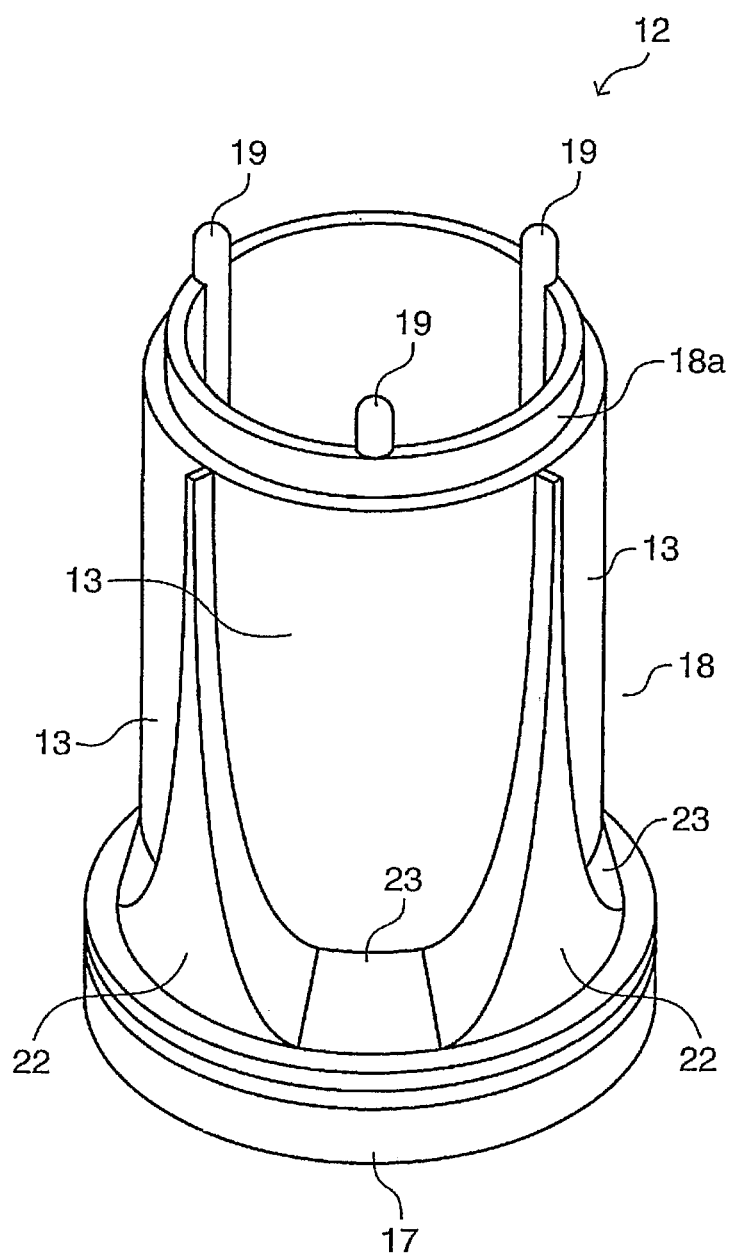
FIG. 11 is a perspective view of a base material body (first embodiment).
Figure 12:
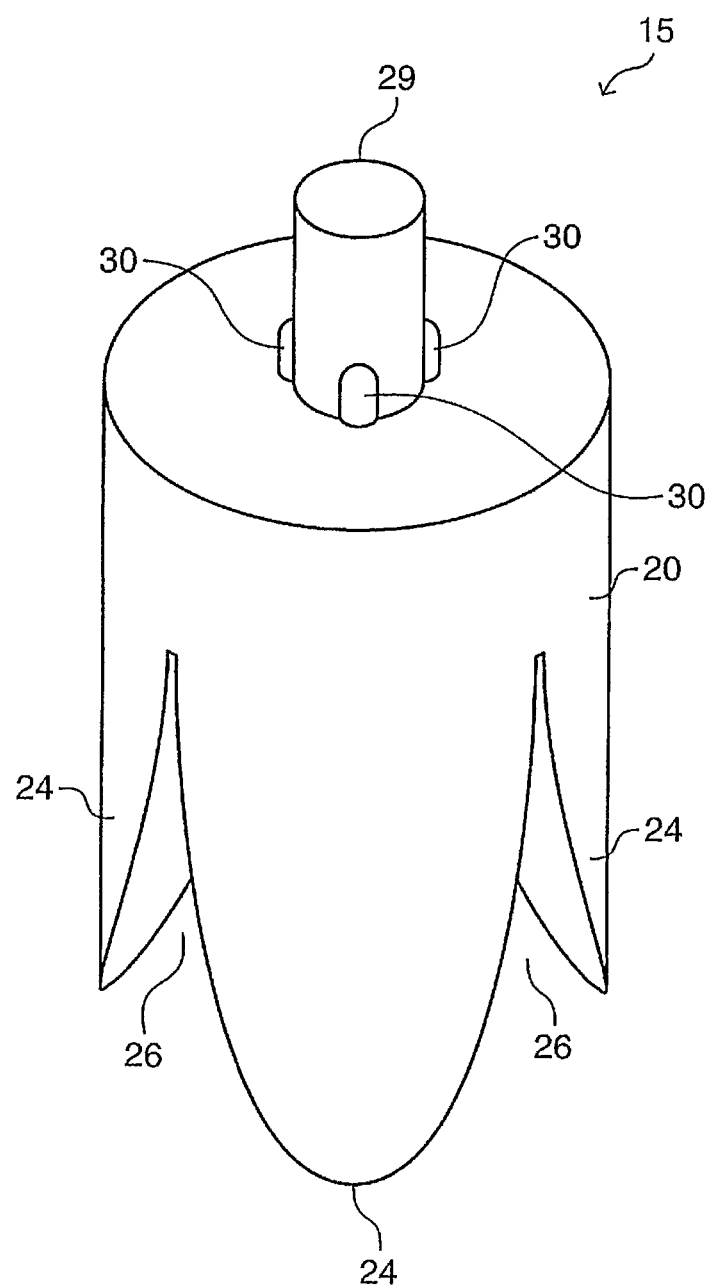
FIG. 12 is a perspective view of an inner cover (first embodiment).
Figure 13:
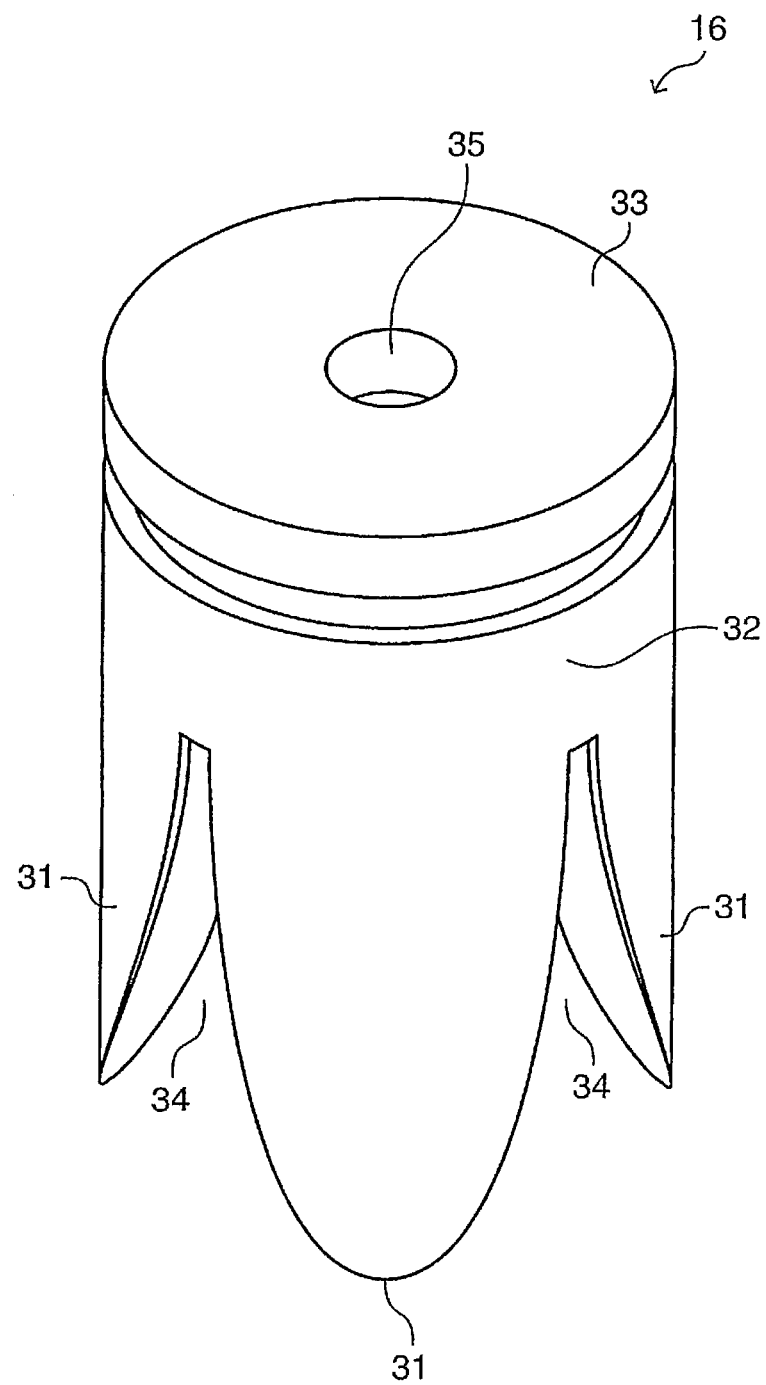
FIG. 13 is a perspective view of an outer cover (first embodiment).

As shown in FIGS. 6 to 8, the inside and the outside of the stent body 4 communicate with each other at the exposed portion 7, and thus the stent body 4 can be indwelled in the ampulla 3 without blocking a branch blood vessel 8 such as a coronary artery branching off from an aortic sinus, and also an area of the blood vessel wall of the blood vessel 2 covered with the stent body 4 is minimized. The stent body 4 spans the ampulla 3 in the blood flow direction, and thus a gap 9 is created between the blood vessel wall of the ampulla 3 and the valved stent 1. When the valve is closed, blood once flows from a wide range of the exposed portion 7 into the gap 9, and then flows into the branch blood vessel 8. This allows the blood in the valved stent 1 to smoothly flow into the branch blood vessel 8, and eliminates the need to accurately align the exposed portion 7 with the branch blood vessel 8.

Figure 2:
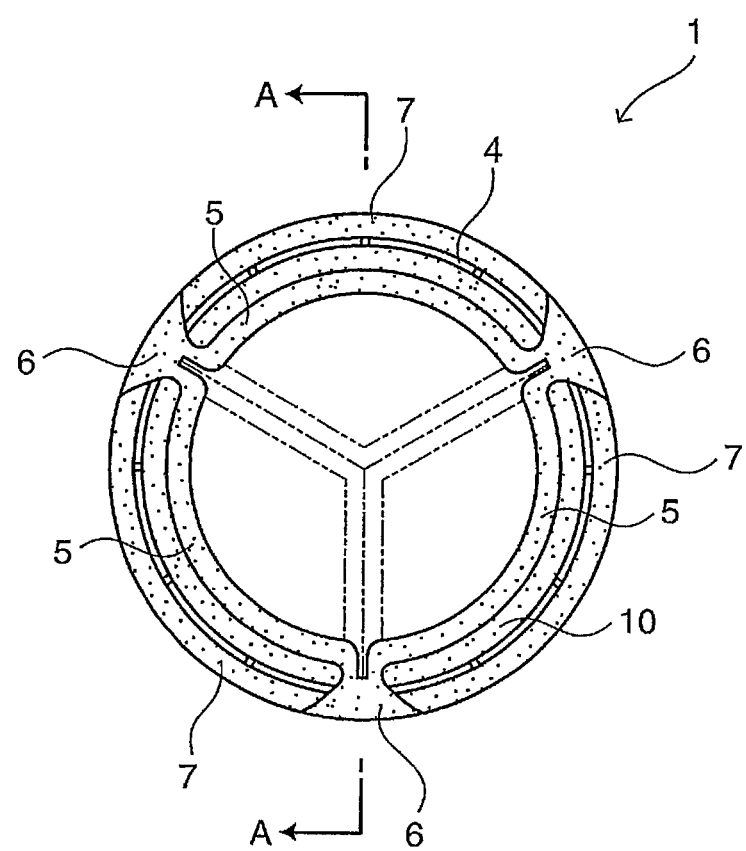
FIG. 2 is a plan view of the valved stent.
Figure 3:
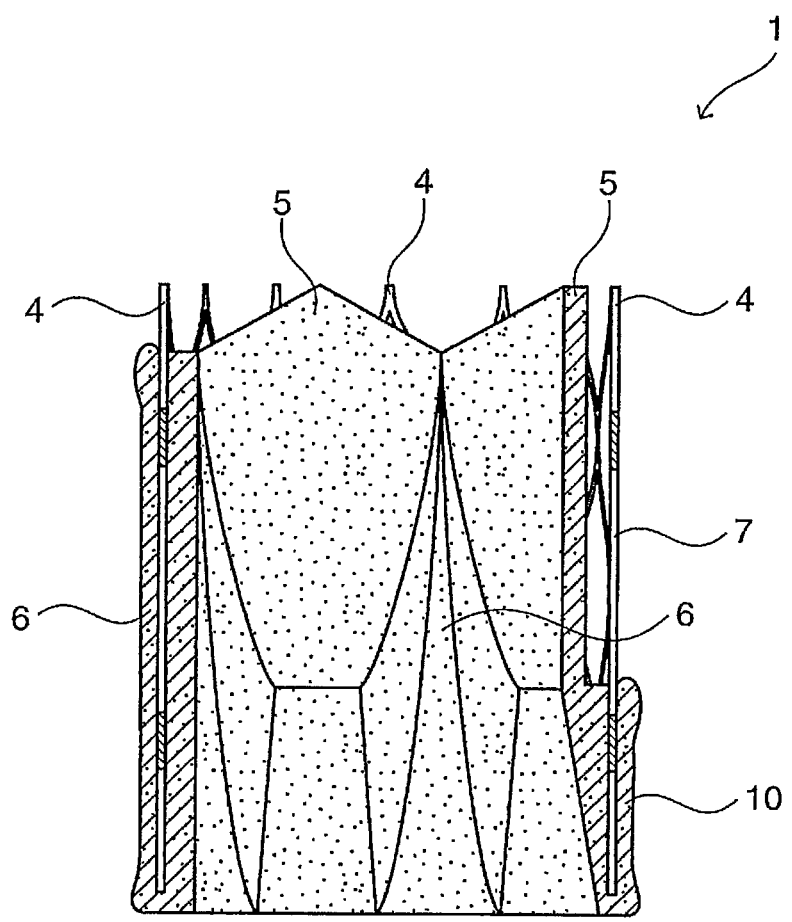
FIG. 3 is an A-A sectional view of FIG. 2, showing a valve being opened.
Figure 4:
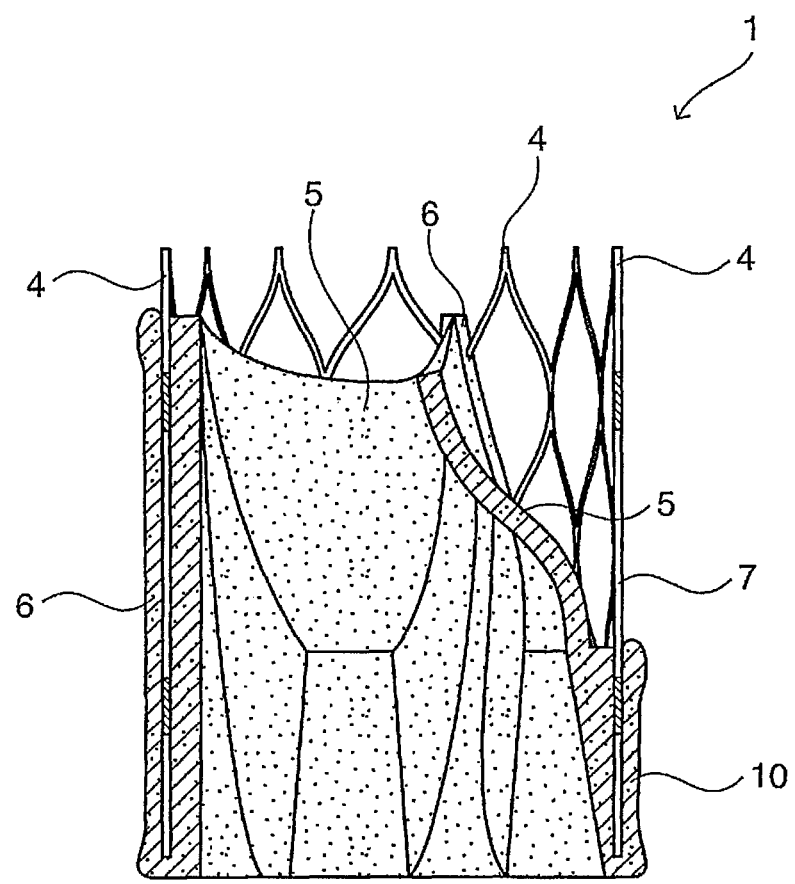
FIG. 4 is an A-A sectional view of FIG. 2, showing a valve being closed.
Figure 5:
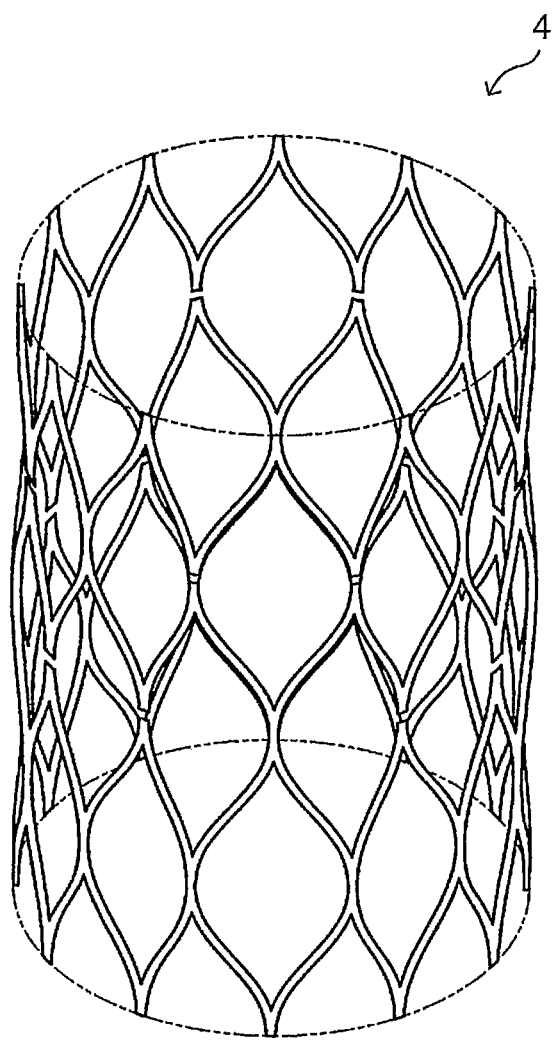
FIG. 5 is a perspective view of a stent body.

A plurality of such leaflets 5 are arranged in parallel in a circumferential direction of the stent body 4, and reciprocate radially inward and outward to function as, for example, an aortic valve having the leaflets 5 that are trileaflet valves and open/close an aorta in the blood flow direction. The plurality of leaflets 5 are integrated at its base end to constitute an annular leaflet base end 10, and the leaflet base end 10 is formed to cover around one end of the stent body 4. Further, opposite sides of each leaflet 5 are secured to the stent body 4 via the connection section 6, and the plurality of leaflets 5 are each integrated with the stent body 4 in three positions at the base end and the opposite sides. In FIG. 2, dash-double-dot lines are phantom lines showing the leaflets 5 being closed.

The contact section 6 is formed continuously in the blood flow direction from the leaflet base end 10 around one end of the stent body 4 to around the other end of the stent body 4. A plurality of such contact sections 6 are formed at intervals in the circumferential direction of the stent body 4 so as to be aligned with a boundary between the plurality of leaflets 5 in the circumferential direction of the stent body 4, and opposite sides of the leaflet 5 are continuous with each contact section 6. Between the plurality of contact sections 6, the exposed portion 7 is provided so as to expose the stent body 4 to provide communication between the inside and the outside of the stent body 4.

Next, a base material 11 for forming a valved stent 11 for forming the above-described valved stent 1 will be described.

As shown in FIGS. 9 to 13, the base material for forming a valved stent 11 is placed in an environment with a body tissue material to form film-like tissue on a surface of the base material and form the valved stent 1, and includes a columnar base material body 12, a plurality of recesses 13 formed in an outer peripheral surface of the base material body 12, an inner cover 15 that covers the recesses 13 to form a leaflet forming space 14 for forming the leaflet 5, and an outer cover 16 placed on an outer surface side of the inner cover 15 with the stent body 4 interposed therebetween.

The base material body 12 includes a cylinder 18 having the plurality of recesses 13 formed in the peripheral surface and a disk-like flange 17 having a larger diameter than the cylinder 18, and is generally formed into a columnar shape with the flange 17 being provided at one end of the cylinder 18. A small diameter portion 18a and a plurality of such protrusions 19 are formed at a front end of the cylinder 18, and the small diameter portion 18a and the protrusions 19 are engaged with a flange 20 of the inner cover 15 to mount the inner cover 15. The flange 17 has an air hole 21 through which air escapes from or to the inside of the cylinder 18 when the inner cover 15 is attached or detached.

The material for the base material body 12 is preferably resin that has strength (hardness) such as not to be significantly deformed when embedded into a living body, has chemical stability and resistance to load such as sterilization, and contains no or little eluate that stimulates the living body, for example, silicone resin or acrylic resin can be mentioned, but is not limited to these. A thickness of the valved stent 1 is determined by the outer diameter of the cylinder 18, and thus the diameter can be changed depending on a desired thickness.

The recesses 13 are set to a depth such that a cylindrical surface including bottom surfaces thereof has a slightly larger diameter than the small diameter portion 18a, and formed with substantially triangular boundaries 22 therebetween in the circumferential direction in a plurality of positions of the cylinder 18 over the entire length except the small diameter portion 18a. A taper 23 is formed in the recess 13 near the flange 17 so that the connective tissue can easily enter the leaflet forming space 14 when the leaflet 5 is formed.

The inner cover 15 is made of, for example, acrylic resin, and includes a plurality of substantially semielliptical cover pieces 24 and a flange 20 having substantially the same diameter as the cylinder 18 of the base material body 12, and the cover pieces 24 protrude from a peripheral edge of the flange 20 toward one surface.

The cover piece 24 covers the recess 13 of the base material body 12 except the peripheral edge to form the leaflet forming space 14, and forms an entry opening through which the connective tissue enters the leaflet forming space 14 near the taper 23. A front end surface of the leaflet forming space 14 is formed by one surface and the peripheral edge of the flange 20, and a groove 25 forming a front end shape of the leaflet 5 is formed in the one surface and the peripheral edge of the flange 20.

An open section 26 that exposes the boundary 22 of the base material body 12 is formed between cover pieces 24 adjacent to each other, and the boundary 22 and the outer surfaces of the cover pieces 24 are included in a common cylindrical surface.

At a center of one surface of the flange 20, a fitting recess 27 in which the small diameter portion 18a of the cylinder 18 of the base material body 12 fits, and a fitting hole 28 in which the protrusion 19 fits are formed. The small diameter portion 18a and the fitting recess 27 constitute a radial positioning section that radially positions the inner cover 15 with respect to the base material body 12. The protrusion 19 and the fitting hole 28 constitute a circumferential positioning section that circumferentially positions the inner cover 15 with respect to the base material body 12.

At a center of the other surface of the flange 20, a fitting shaft 29 is formed to protrude, and a plurality of protrusions 30 are formed around a base end of the fitting shaft 29 so that the fitting shaft 29 and the protrusion 30 are engaged with the outer cover 16 to mount the outer cover 16 to the inner cover 15.

The outer cover 16 is made of, for example, acrylic resin, and includes a plurality of substantially semielliptical cover pieces 31, a cylinder 32 having substantially the same diameter as the flange 17 of the base material body 12 and covering an outer peripheral side of the flange 20 of the inner cover 15, and a flange 33 having substantially the same diameter as the flange 17 of the base material body 12. In the outer cover 16, the cylinder 32 protrudes from a peripheral edge of the flange 33 toward one side, and further the cover piece 31 protrudes from one end of the cylinder 32.

The cover piece 31 has substantially the same shape as the cover piece 24 of the inner cover 15, and covers the outer surface of the cover piece 24 via the stent body 4. The cover piece 31 prevents the connective tissue from entering between the cover piece 31 and the cover piece 24 of the inner cover 15, and forms the exposed portion 7 in a region of the stent body 4 between the cover pieces 24 and 31.

An open section 34 that exposes the boundary 22 of the base material body 12 is formed between cover pieces 31 adjacent to each other. The open sections 26 and 34 of the inner cover 15 and the outer cover 16 expose the boundary 22 of the base material body 12 via the stent body 4, and allow the connective tissue to enter the outer surface side of the boundary 22 to form the contact section 6 of the valved stent 1.

At a center of the flange 33, a fitting bore 35 in which the fitting shaft 29 of the inner cover 15 fits is formed, and fitting holes 36 in which the protrusions 30 of the inner cover 15 fit are formed around the fitting bore 35. The fitting shaft 29 and the fitting bore 35 constitute a radial positioning section that radially positions the outer cover 16 with respect to the inner cover 15. The protrusions 30 and the fitting holes 36 constitute a circumferential positioning section that circumferentially positions the outer cover 16 with respect to the inner cover 15.

Next, a method for producing the valved stent 1 using the above-described base material for forming a valved stent 11 will be described.

This production method includes: an "assembly step" of assembling the base material for forming a valved stent 11 by incorporating the stent body 4 between the inner cover 15 and the outer cover 16; a "placement step" of placing the base material for forming a valved stent 11 in an environment with a body tissue material; a "formation step" of forming film-like tissue 37 around the base material for forming a valved stent 11; a "taking-out step" of taking out the base material 11 for forming a valved stent covered with the tissue 37 from the environment; and a "separation step" of integrally delaminating and taking out the tissue 37 including the leaflet 5 and the stent body 4 from the base material 11 for forming a valved stent as the valved stent 1.

<Assembly Step>

Figure 14:
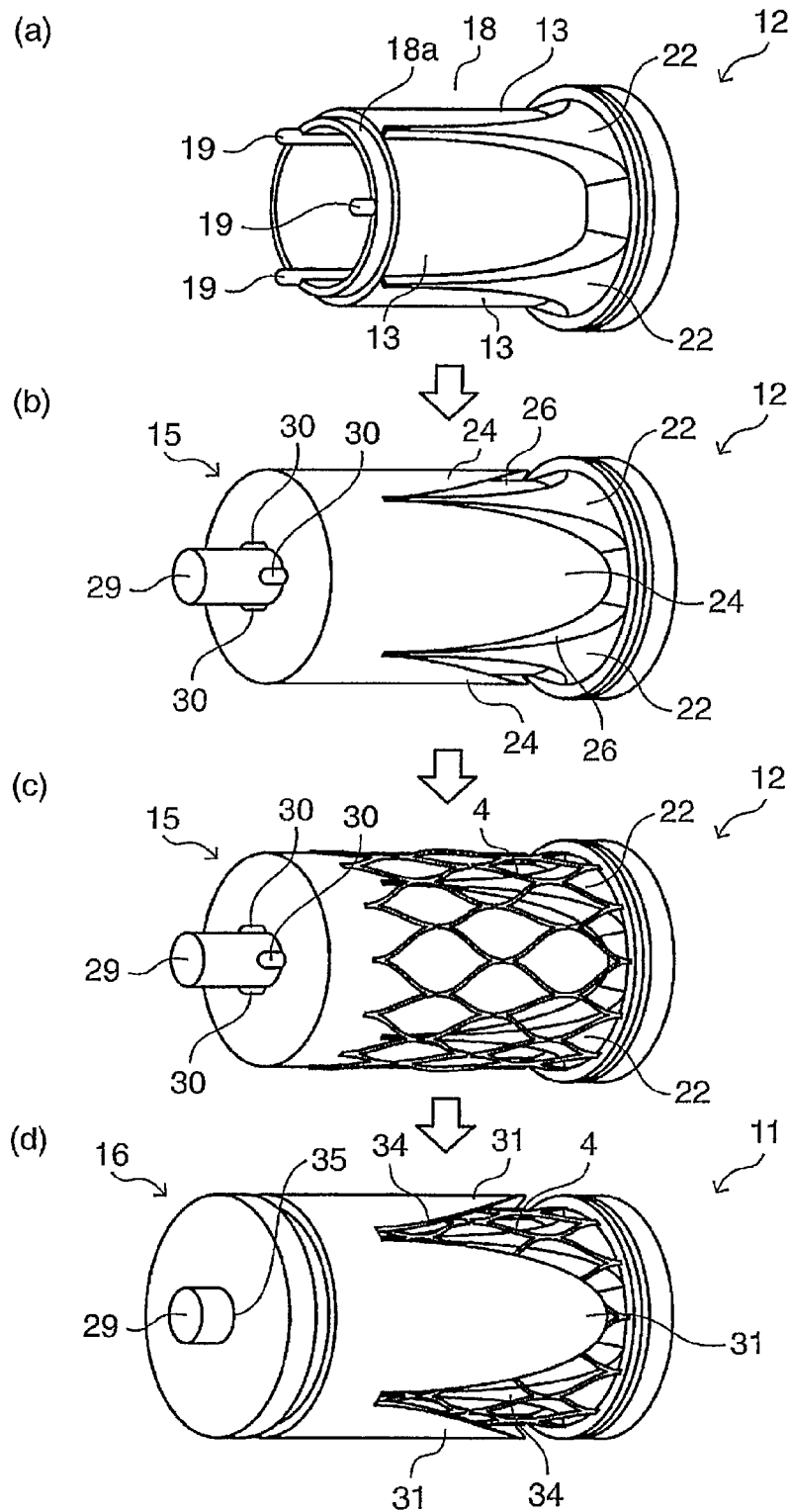
FIG. 14 illustrates a procedure for assembling the base material for forming a valved stent (first embodiment).

The inner cover 15 is central-axially placed over the base material body 12, the small diameter portion 18a and the protrusion 19 at the front end of the base material body 12 are fitted in the fitting recess 27 and the fitting hole 28 of the inner cover 15 to mount the inner cover 15 to the base material body 12 (FIGS. 14(a) and (b)). Thus, the inner cover 15 is radially and circumferentially positioned with respect to the base material body 12, and the recess 13 in the base material body 12 is covered with the cover piece 24 of the inner cover 15 to form the leaflet forming space 14.

Then, the stent body 4 is placed outside the inner cover 15 (FIG. 14(c)), the outer cover 16 is further placed over the stent body 4, the fitting shaft 29 and the protrusions 30 of the inner cover 15 are fitted in the fitting bore 35 and the fitting holes 36 in the outer cover 16, and the outer cover 16 is mounted to the inner cover 15 (FIG. 14(d)). Thus, the outer cover 16 is radially and circumferentially positioned with respect to the inner cover 15, the cover piece 24 of the inner cover 15 is covered with the cover piece 31 of the outer cover 16, the cover pieces 24 and 31 hold the stent body 4 therebetween, and the open sections 26 and 34 in the inner cover 15 and the outer cover 16 expose the boundary 22 of the base material body 12 via the stent body 4.

<Placement Step>

Figure 15:
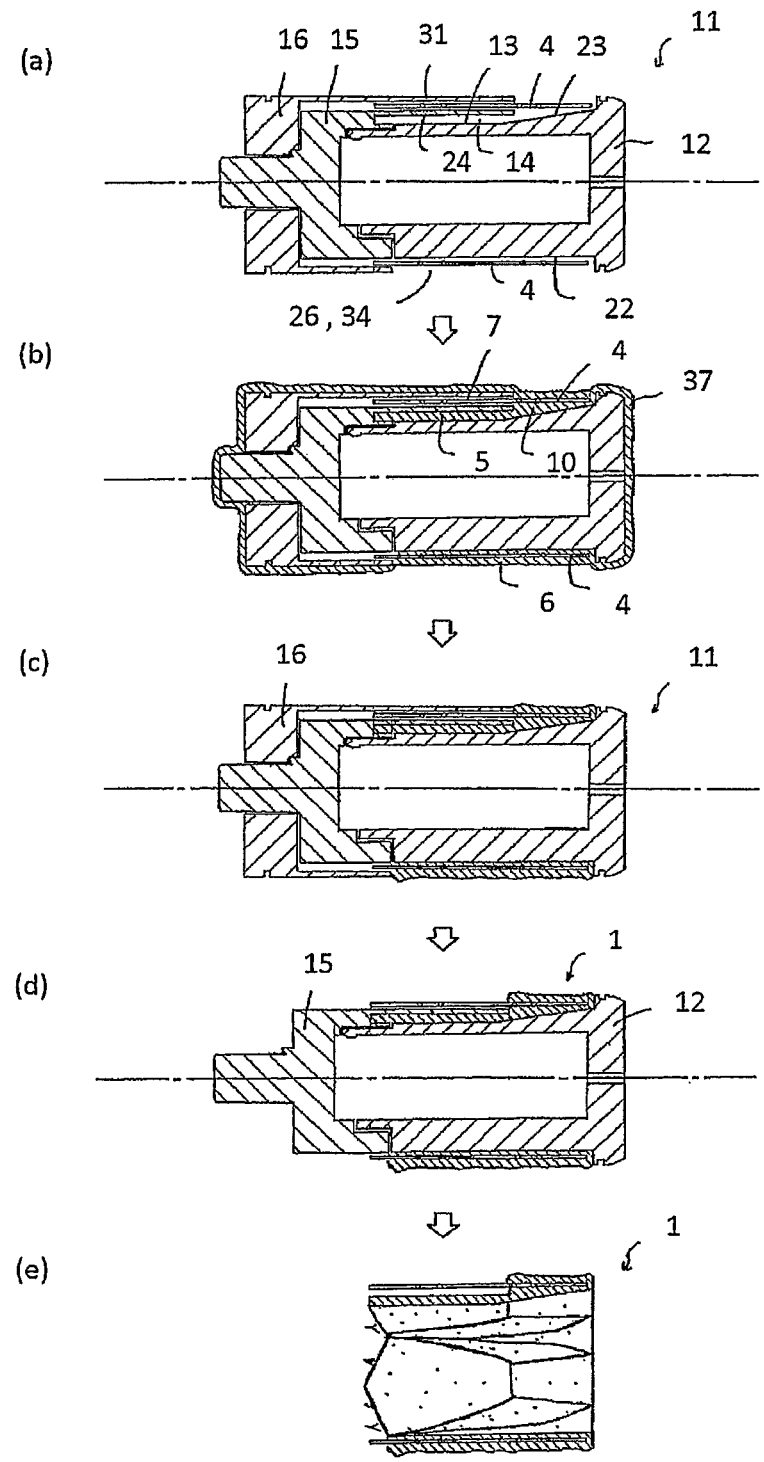
FIG. 15 illustrates a procedure for forming the valved stent (first embodiment).

The base material for forming a valved stent 11 is placed in an environment with a body tissue material (FIG. 15(a)). The wording "in the environment with a body tissue material" refers to an inside of a living body (for example, embedding under skin or into abdominal cavity) of animals or to an artificial environment such as a solution in which a body tissue material is suspended outside a living body of animals. The body tissue material includes materials derived from mammals such as humans, dogs, cows, pigs, goats, rabbits or sheep, or birds, fish, and other animals, and artificial materials.

The base material 11 for forming a valved stent 11 is embedded into animals with a minimum incision under sufficient anesthesia, and a wound is stitched up after the embedding. The base material 11 for forming a valved stent is preferably embedded into, for example, an abdominal cavity having a capacity that receives the base material for forming a valved stent 11, or under skin of four limbs, shoulder, back, abdomen, or the like. Embedding is preferably performed by a less invasive method with a minimum incision under sufficient anesthesia in a spirit of animal protection.

When the base material 11 for forming a valved stent is placed in the environment with a body tissue material, various cultivation conditions may be adjusted to perform cell culture in a clean environment according to a known method.

<Formation Step>

After the placement step, a predetermined period of time passes, and then the film-like tissue 37 is formed around the base material for forming a valved stent 11 (FIG. 15(b)). The tissue 37 is composed of fibroblasts and extracellular matrix such as collagen.

One part of the tissue 37 enters the leaflet forming space 14 through the entry opening between the front end of the cover piece 24 of the inner cover 15 and the taper 23 of the recess 13 to form the leaflet 5, and the leaflet 5 is integrated with the stent body 4 via the contact section 6, and the leaflet base end 10 formed at the entry opening. The other part of the tissue 37 covers the boundary 22 exposed from the open sections 26 and 34 in the inner cover 15 and the outer cover 16 to form the contact section 6 integrated with the stent body 4, and the contact section 6 and the opposite edges of the leaflet 5 are continuous between the cover piece 24 and the opposite sides of the recess 13.

<Taking-Out Step>

After the tissue 37 is sufficiently formed through the formation step for the predetermined period of time, the taking-out step of taking out the base material for forming a valved stent 11 from the environment with a body tissue material is performed. The base material for forming a valved stent 11 taken out from the environment with a body tissue material is entirely covered with a film of body tissue. However, the tissue 37 does not enter between the cover pieces 24 and 31 of the inner cover 15 and the outer cover 16, and the exposed portion 7 is formed in a region of the stent body 4 between the cover pieces 24 and 31.

<Separation Step>

The tissue 37 on the surfaces of the opposite ends of the base material for forming a valved stent 11 and the outer cover 16 is removed (FIG. 15(c)), the outer cover 16 is detached (FIG. 15(d)), then the base material body 12 and the inner cover 15 are central-axially disassembled and taken out from a lumen of the valved stent 1 to obtain the valved stent 1 (FIG. 15(e)).

For heterotransplantation of the produced valved stent 1, elimination of immunogen such as decellularization, dehydration, or fixing is preferably performed to avoid rejection after transplantation. The decellularization includes ultrasonic treatment, surfactant treatment, eluting extracellular matrix by enzyme treatment with collagenase or the like and washing, or the like. The dehydration includes washing with a water-soluble organic solvent such as methanol, ethanol, or isopropyl alcohol. The fixing includes treatment with an aldehyde compound such as glutaraldehyde or formaldehyde.

This embodiment is not limited to the above, but changes may be made within the scope of the present invention. For example, there is no need to align the opposite ends of the stent body 4 with the opposite ends of the leaflet 5 and the contact section 6 as described above, but one end and/or the other end of stent body 4 may protrude from the leaflet 5 and the contact section 6 in the blood flow direction. In particular, the other end of the stent body 4 may protrude from the front ends of the leaflet 5 and the contact section 6, thereby allowing contact with the blood vessel wall in a wide range, and causing less displacement of the valved stent 1. Further, the protruding region of the stent body 4 is increased in diameter to allow the valved stent 1 to be more reliably attached to the blood vessel 2.

The valved stent 1 is indwelled in the aortic sinus to function as an aortic valve, and may also be indwelled in a pulmonary artery to function as a pulmonary valve.

Second Embodiment

This embodiment is substantially the same as the first embodiment, but a reverse valved stent 38 with an inside and an outside being reversed of a valved stent 1 is once formed, and is reversed to form the valved stent 1. First, a base material for forming a valved stent 39 will be described.

Figure 16:
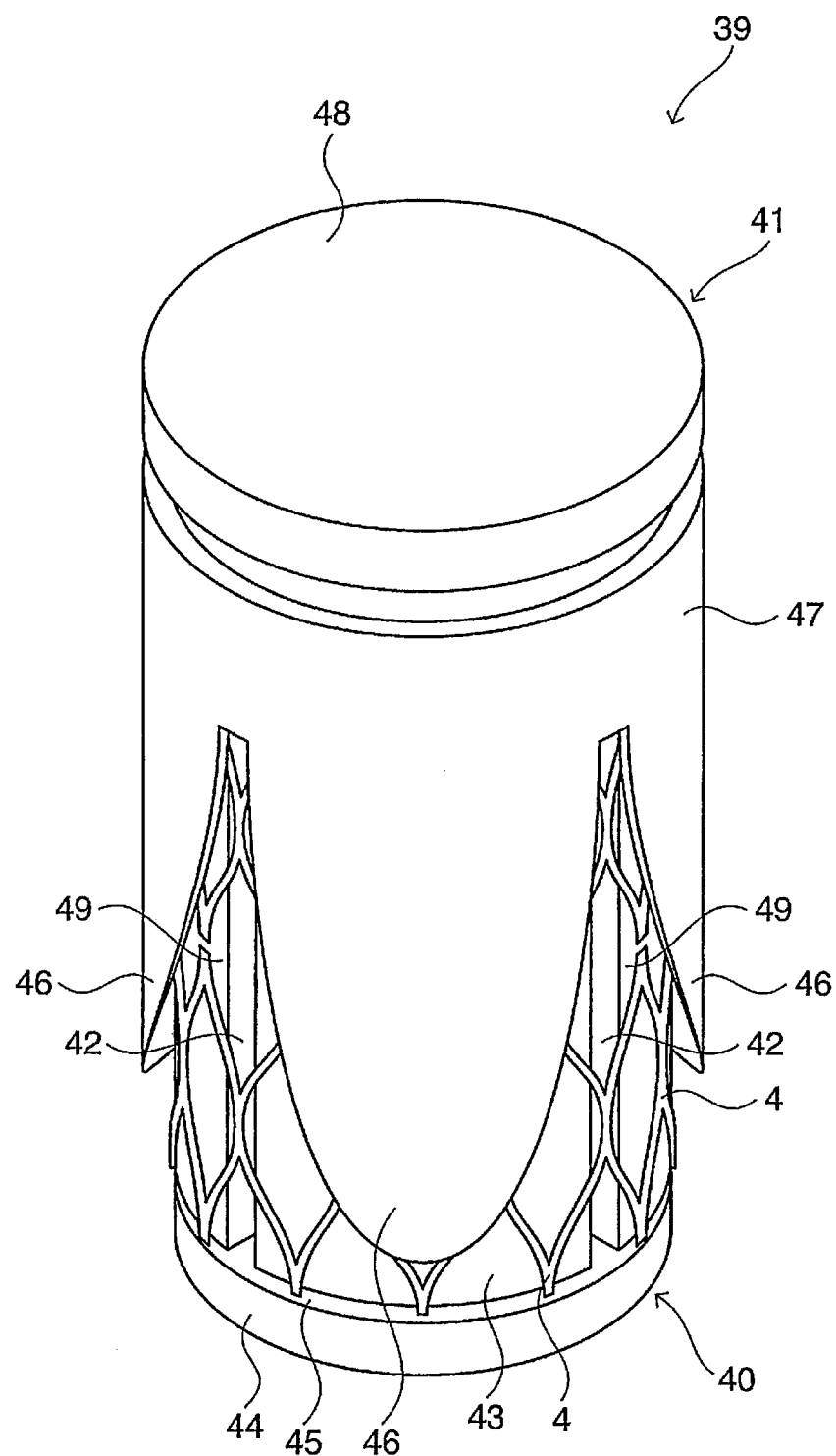
FIG. 16 is a perspective view of a base material for forming a valved stent (second embodiment).
Figure 17:
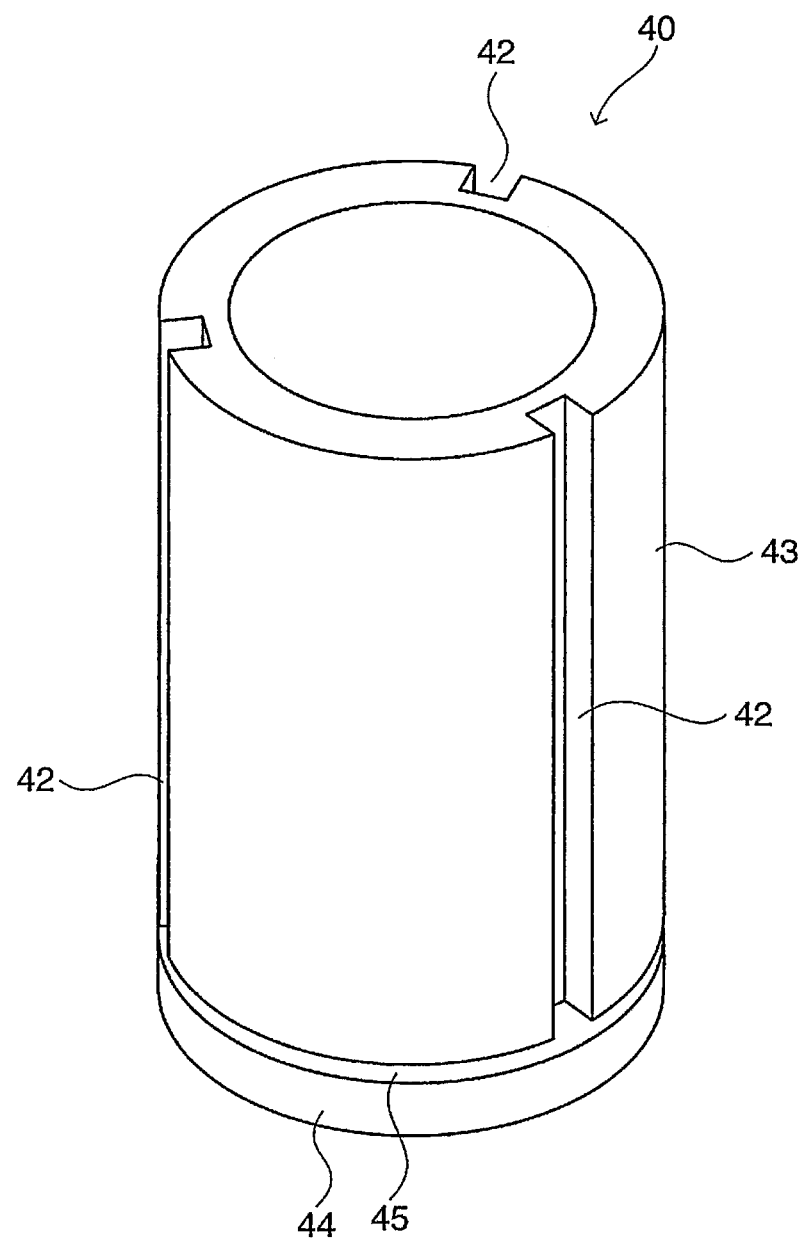
FIG. 17 is a perspective view of a base material body (second embodiment).
Figure 18:
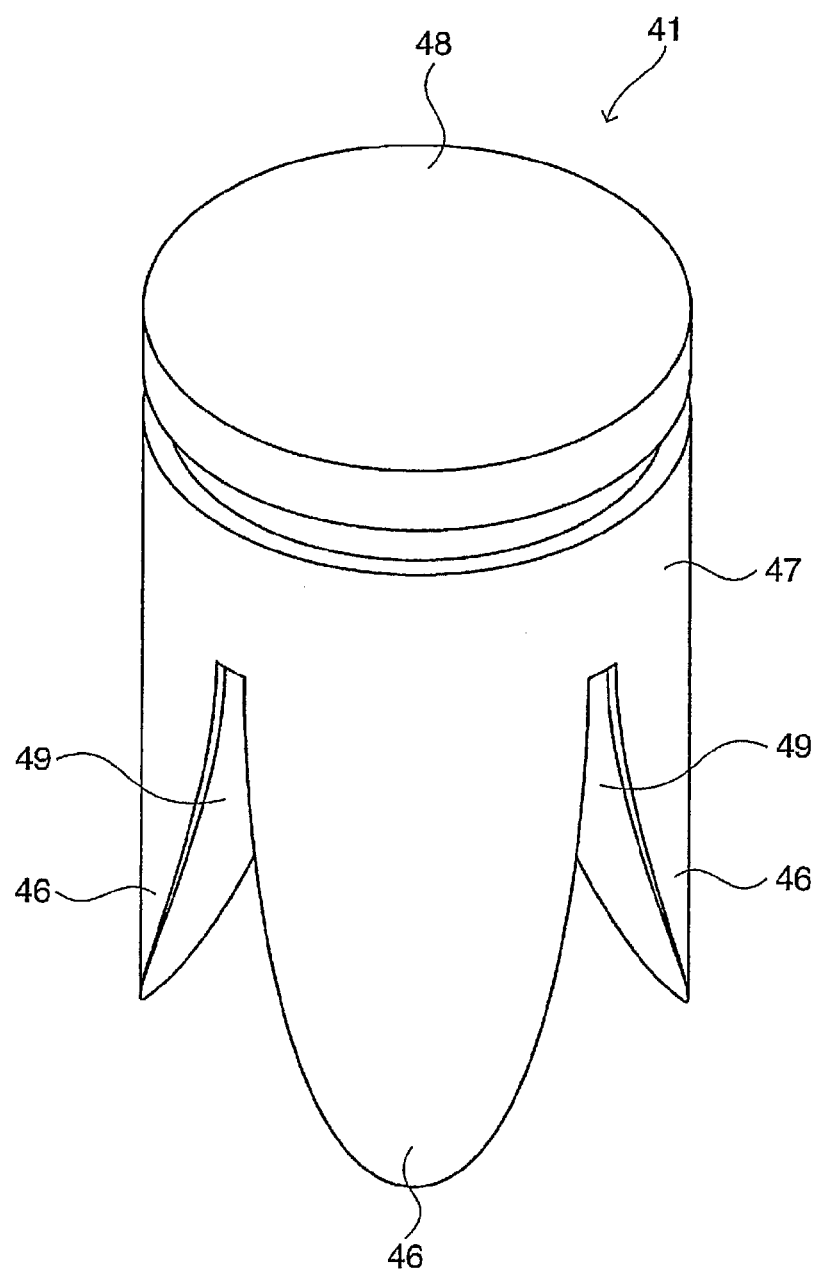
FIG. 18 is a perspective view of a base material cover (second embodiment).

As shown in FIGS. 16 to 18, the base material for forming a valved stent 39 is placed in an environment with a body tissue material, and thus film-like tissue 37 is formed on a surface of the base material to form the reverse valved stent 38, and includes a columnar base material body 40, and a base material cover 41 placed on an outer peripheral side of the base material body 40 via a stent body 4.

The base material body 40 includes a cylindrical cylinder 43 having a plurality of entry grooves 42 parallel to a central axis formed over the entire length in its outer peripheral surface, and a disk-like base 44 having substantially the same diameter as the cylinder 43, and is generally formed into a columnar shape with the base 44 being formed at one end of the cylinder 43 via a peripheral groove 45.

The base material cover 41 includes a plurality of substantially semielliptical cover pieces 46, a cylinder 47 sized to be externally fitted to the cylinder 43 of the base material body 40 via the stent body 4, and a flange 48 having substantially the same diameter as the cylinder 47. In the base material cover 41, the flange 48 is provided at one end of the cylinder 47, the cover pieces 46 are formed to protrude from the other end of the cylinder 47, and a total length of the cover piece 46 and the cylinder 47 is slightly shorter than a length of the cylinder 43 of the base material body 40.

A substantially triangular open section 49 that exposes the outer peripheral surface of the base material body 40 via the stent body 4 is formed between the cover pieces 46 adjacent to each other, and the base material cover 41 is placed outside the base material body 40 so that the open section 49 is circumferentially aligned with the entry groove 42.

The open section 49 exposes the stent body 4 provided between the base material body 40 and the base material cover 41, and exposes the entry groove 42 in the base material body 40 via the stent body 4. Thus, connective tissue formed around the base material 39 for forming a valved stent forms a leaflet 5 on an outer surface side of the cover piece 46, enters the entry groove 45 from the open section 49 through the stent body 4, and is integrated with the stent body 4 at the inside and the outside thereof to form a contact section 6. The entry groove 45 may be formed into a substantially triangular shape to match the shape of the open section 49 so that the stent body 4 and the contact section 6 are more firmly integrated in a wide range.

Next, a method for producing the valved stent 1 using the above-described base material for forming a valved stent 39 will be described.

This production method is substantially the same as in the first embodiment, and includes an "assembly step," a "placement step," a "formation step," a "taking-out step," and a "separation step," but the "assembly step" to the "separation step" are steps for forming the reverse valved stent 38, and after the "separation step," a "reverse step" of obtaining the valved stent 1 from the reverse valved stent 38 is provided.

<Assembly Step>

The stent body 4 is placed outside the cylinder 43 of the base material body 40, and central-axially positioned so that the stent body 4 does not reach the peripheral groove 45 in the base material body 40, the base material cover 41 is placed over the stent body 4 from the front end side of the base material body 40, and the entry groove 45 in the base material body 40 is circumferentially aligned with the open section 49 of the base material cover 41. Thus, a part of the stent body 4 is exposed from the open section 49, the entry groove 42 is exposed via the stent body 4, and the base material 39 for forming a valved stent is assembled with the stent body 4 being integrated between the base material body 40 and the base material cover 41 (FIG. 19(a)).

The stent body 4 is incorporated into the base material 39 for forming a valved stent in a reversed manner, and thus when the reverse valved stent 38 is reversed to obtain the valved stent 1, the stent body 4 can be returned to the original state.

<Placement Step>

As in the first embodiment, the base material 39 for forming a valved stent is placed in an environment with a body tissue material.

<Formation Step>

Figure 19:
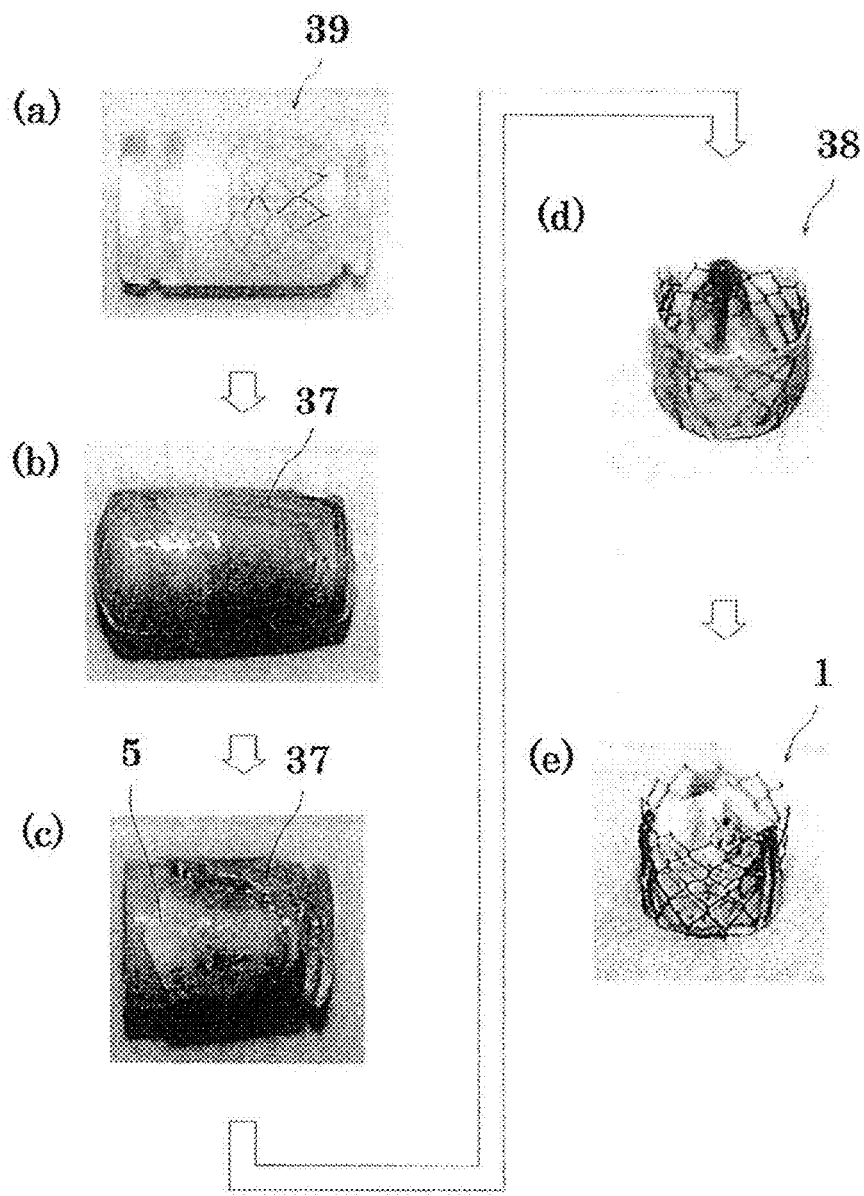
FIG. 19 is a photograph illustrating a procedure for forming the valved stent (second embodiment).

As in the first embodiment, after the placement step, a predetermined period of time passes, and then film-like tissue 37 is formed around the base material 39 for forming a valved stent (FIG. 19(b)).

The tissue 37 covers the outer surface of the base material cover 41 to form the leaflet 5, as well as covers a portion of the cylinder 43 of the base material body 40 exposed from the front end of the cover piece 46 to form a leaflet base end 10, and covers the outside of the stent body 4 exposed from the open section 49. Further, a part of the tissue 37 enters the entry groove 45 through the stent body 4 to form the contact section 6 integrated with the stent body 4, and the leaflet 5 is integrated with the stent body 4 via the contact section 6 and the leaflet base end 10.

<Taking-Out Step>

As in the first embodiment, after the tissue 37 is sufficiently formed, the base material 39 for forming a valved stent covered with the tissue 37 is taken out from the environment with a body tissue material.

<Separation Step>

The tissue 37 on the surfaces of the opposite ends of the base material 39 for forming a valved stent is removed (FIG. 19(c)). At this time, the tissue 37 is removed so as to expose the peripheral groove 45 at one end, and the tissue 37 is removed so as to form the front end of the leaflet 5 into a predetermined shape at the other end.

Then, the base material body 40 and the base material cover 41 are central-axially disassembled, the base material cover 41 is taken out from between the leaflet 5 and the stent body 4, and the base material body 40 is taken out from a lumen of the reverse valved stent 38. Thus, the tissue 37 including the leaflet 5 and the stent body 4 are integrally delaminated from the base material 39 for forming a valved stent to obtain the reverse valved stent 38 having the leaflet 5 on the outer peripheral side of the stent body 4 (FIG. 19(d)).

<Reverse Step>

The inside and the outside of the taken-out reverse valved stent 38 is reversed to obtain the valved stent 1 having the leaflet 5 on an inner peripheral side of the stent body 4 (FIG. 19(e)). At this time, the reverse valved stent 38 is appropriately cooled to reduce elasticity of the stent body 4, thereby facilitating reversing of the reverse valved stent 38.

Other configurations are the same as in the first embodiment.

Third Embodiment

Figure 20:
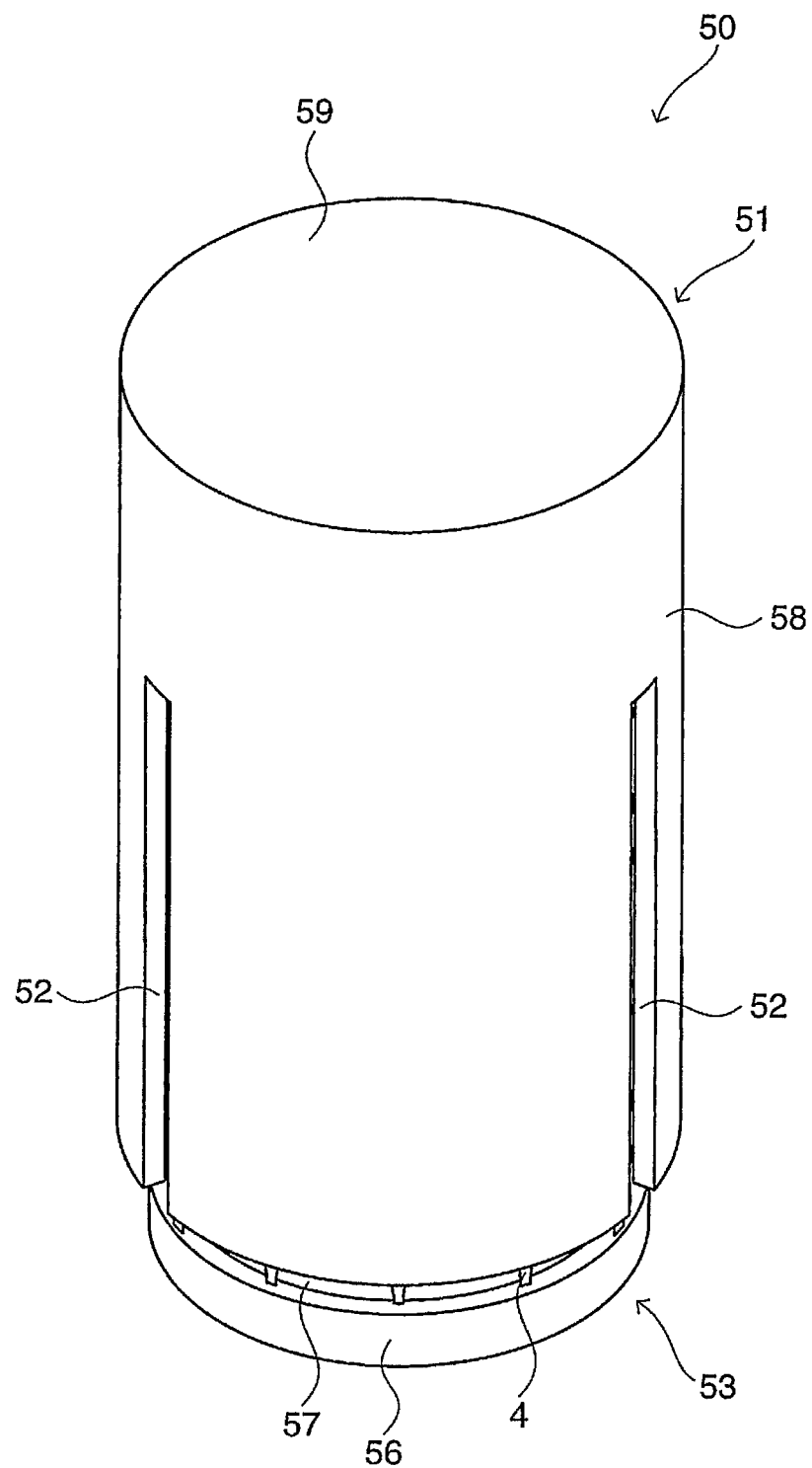
FIG. 20 is a perspective view of a base material for forming a valved stent (third embodiment).
Figure 21:
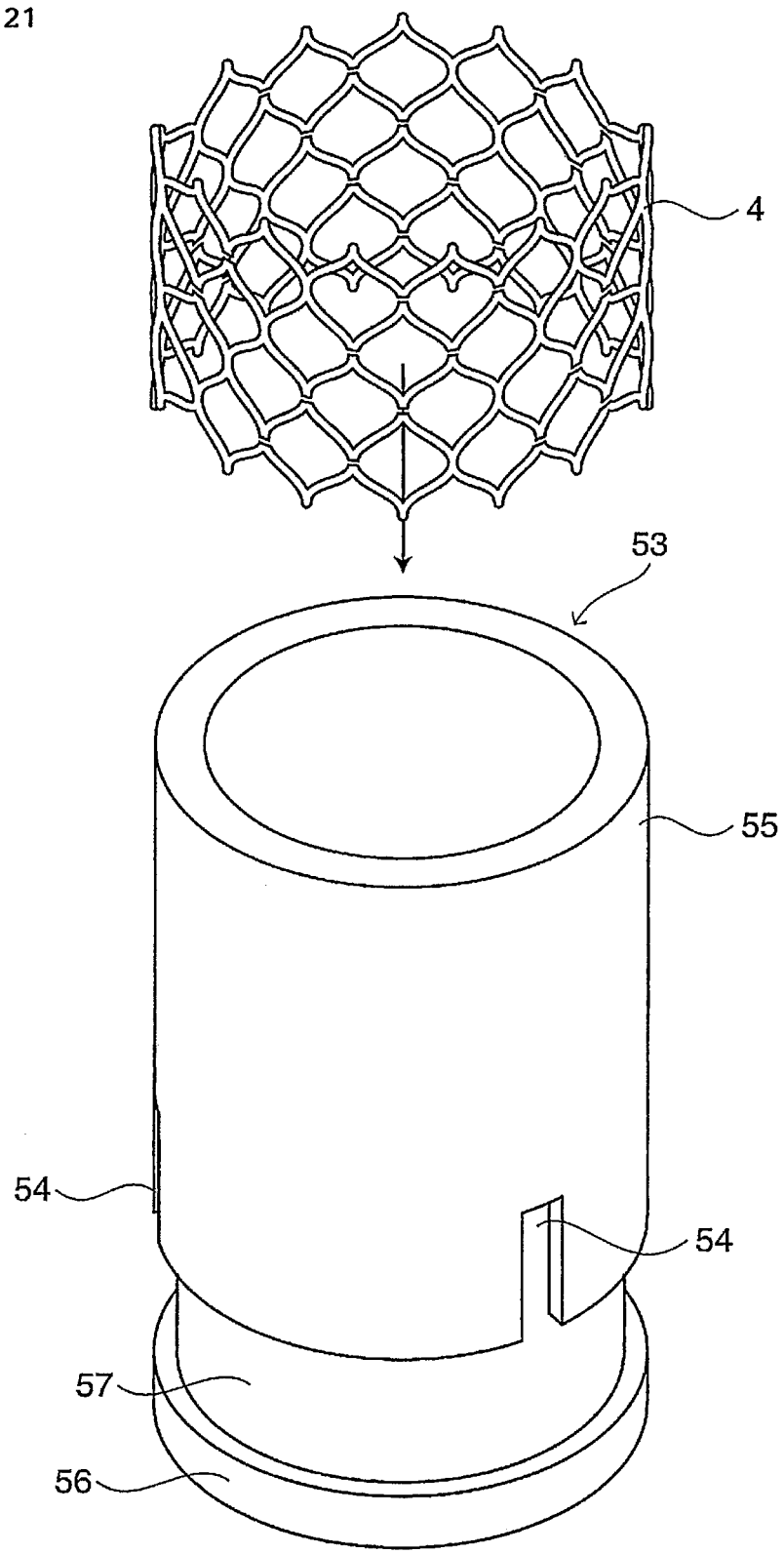
FIG. 21 is a perspective view of a base material body (third embodiment).
Figure 22:
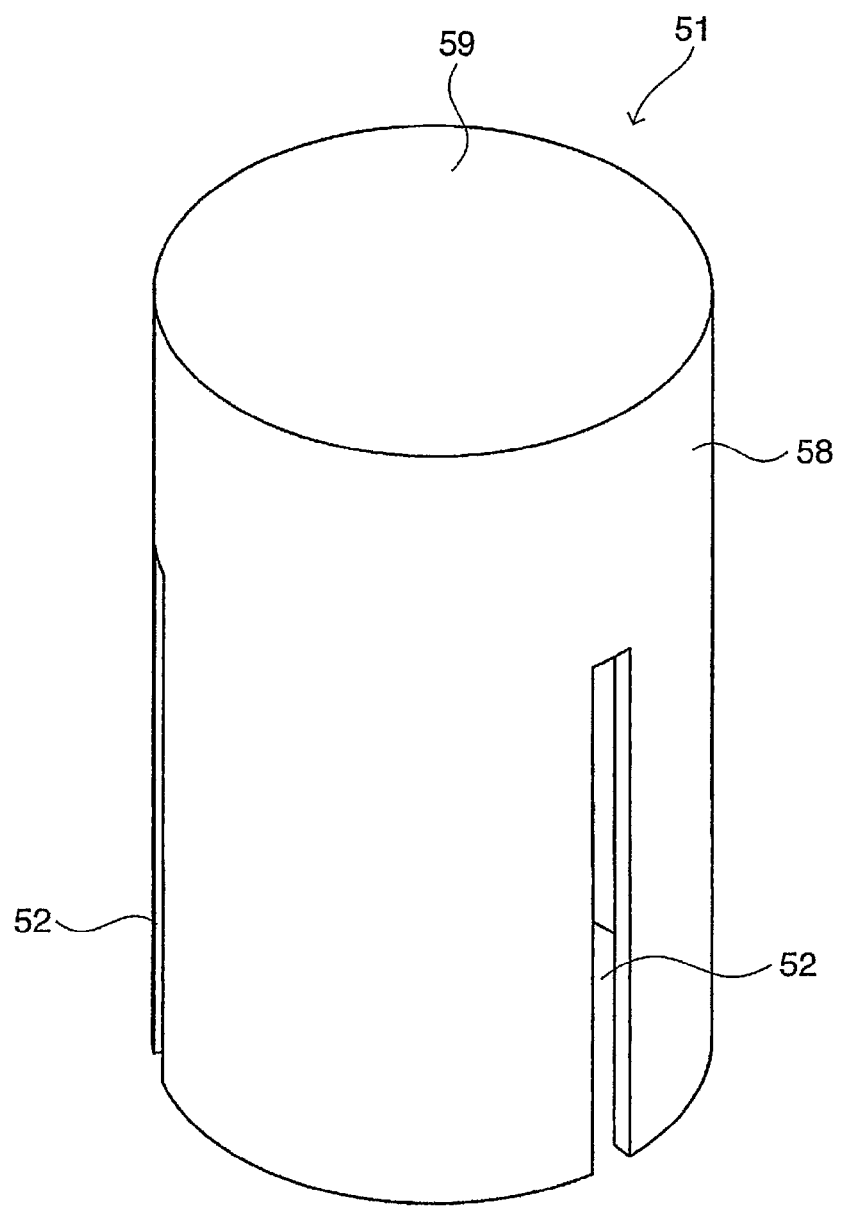
FIG. 22 is a perspective view of a base material cover (third embodiment).

This embodiment is substantially the same as the second embodiment, but instead of forming the substantially triangular open section 49 in the base material cover 41 of the base material 39 for forming a valved stent, as shown in FIGS. 20 to 22, a slit-like open section 52 is formed in a base material cover 51 of a base material 50 for forming a valved stent.

The base material body 53 includes a cylindrical cylinder 55 having a plurality of entry grooves 54 parallel to a central axis formed in an outer peripheral surface, and a disk-like base 56 having substantially the same diameter as the cylinder 55, and is generally formed into a columnar shape with the base 56 being provided at one end of the cylinder 55 via a peripheral groove 57. The entry groove 54 in the base material body 53 is formed in a range from the peripheral groove 57 to around a center of the cylinder 55. The peripheral groove 57 is wider than the peripheral groove 45 in the second embodiment, the stent body 4 is placed to reach the peripheral groove 57, and connective tissue enters the peripheral groove 57 to form a leaflet base end 10.

The base material cover 51 has a flange 59 at one end of the cylinder 58, the slit-like open section 52 is formed in a range from the other end of the cylinder 58 to around the center, and the open section 52 has substantially the same size as the entry groove 54. The cylinder 58 of the base material cover 51 is longer than the cylinder 55 of the base material body 53, and with the cylinder 58 of the base material cover 51 being placed over the cylinder 55 of the base material body 53, the front end of the cylinder 58 of the base material cover 51 covers a part of the peripheral groove 57 of the base material body 53.

The slit-like open section 52 is formed instead of the substantially triangular open section 49 to reduce a force to integrate the contact section 6 formed in the open section 52 with the stent body 4, but the contact section 6 hardly prevents deformation such as a reduction in diameter of the stent body 4, thereby facilitating insertion of the valved stent 1 into a blood vessel or the like. Other configurations are the same as in the second embodiment.

Fourth Embodiment

Figure 23:
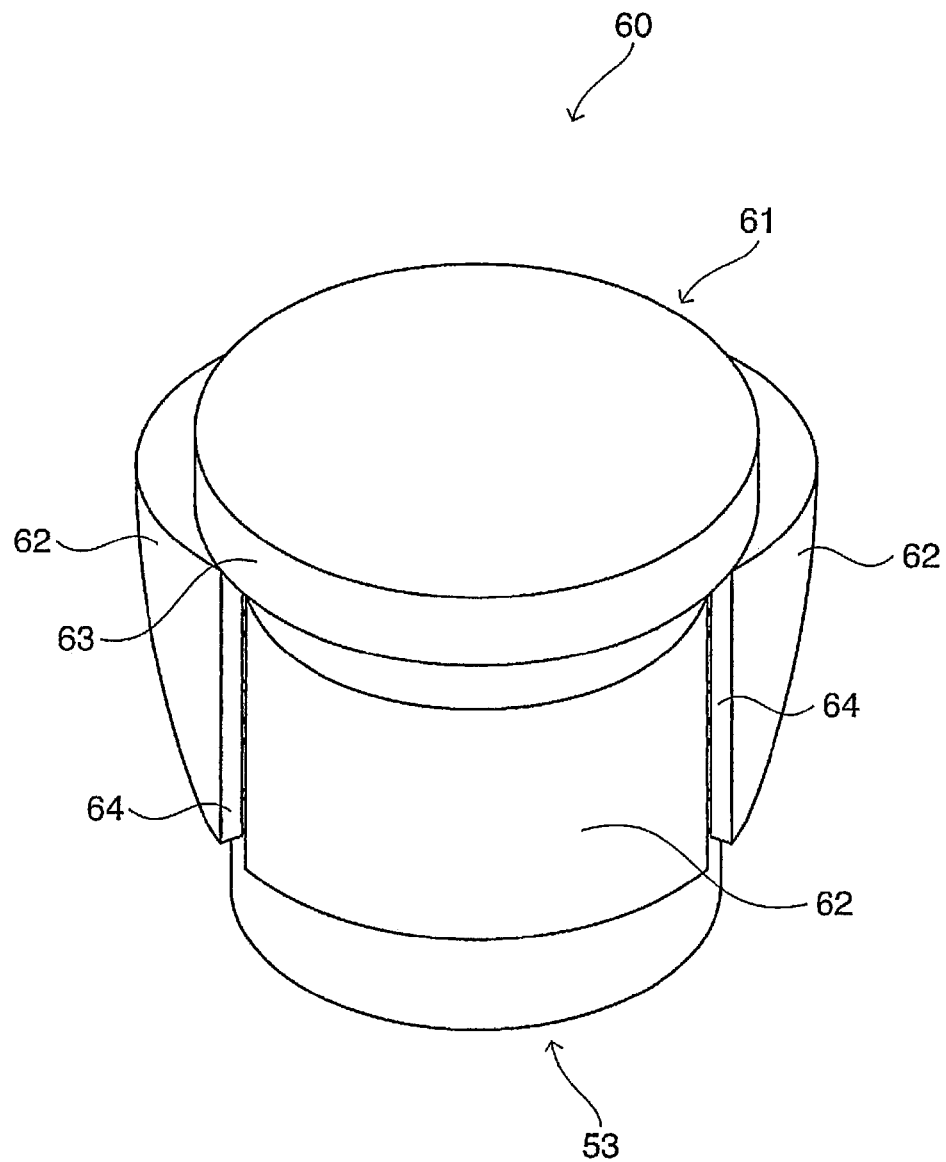
FIG. 23 is a perspective view of a base material for forming a valved stent (fourth embodiment).
Figure 24:
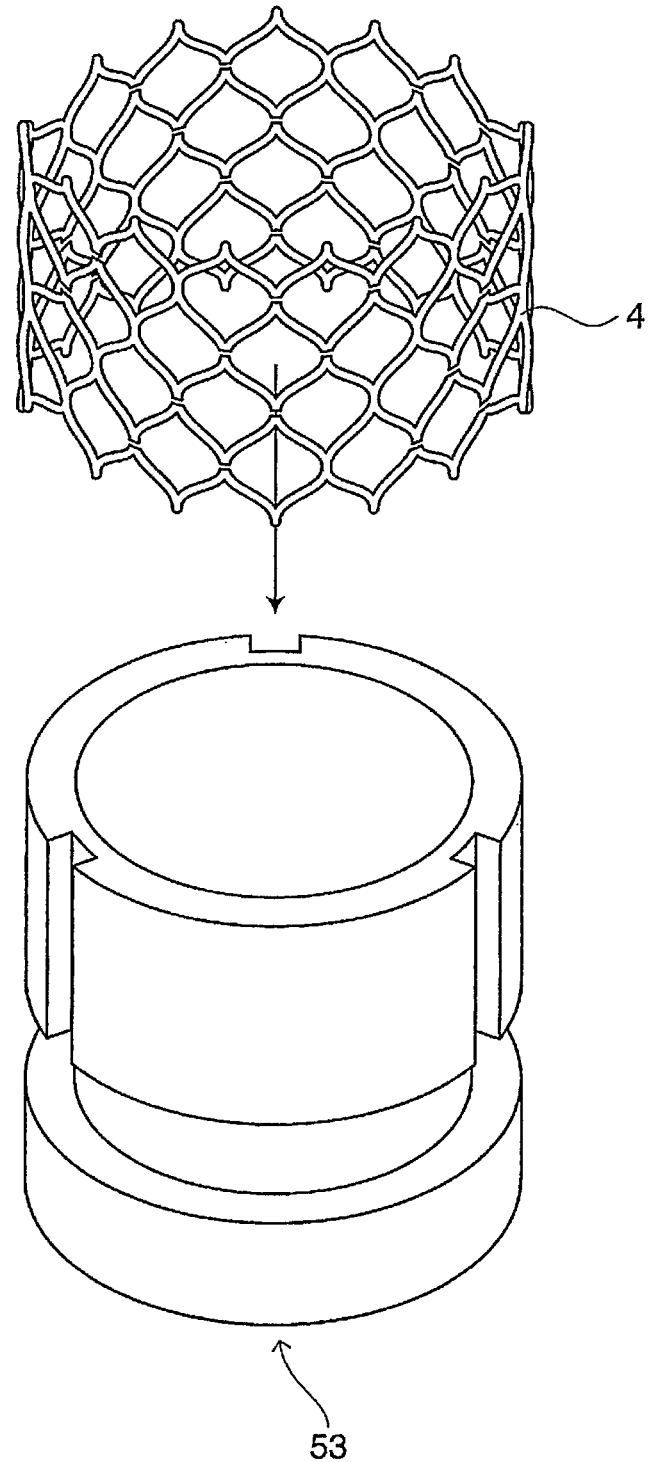
FIG. 24 is a perspective view of a base material body (fourth embodiment).
Figure 25:
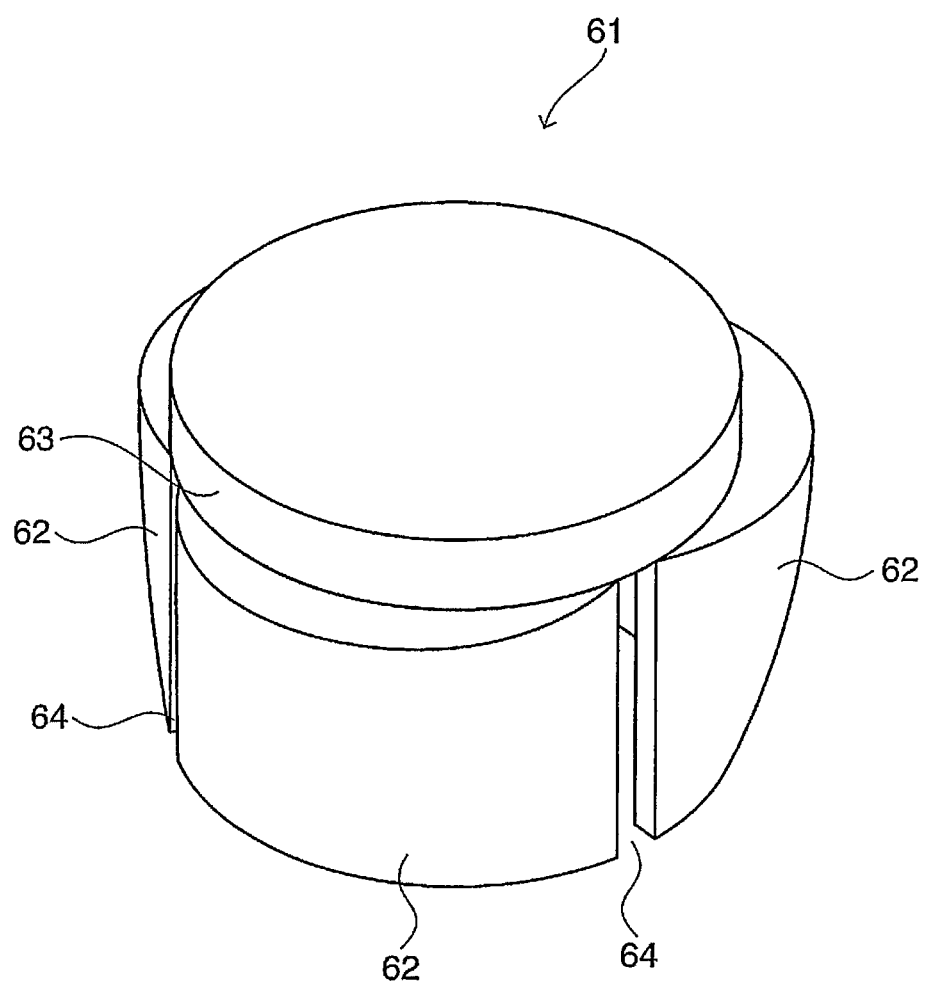
FIG. 25 is a perspective view of a base material cover (fourth embodiment).

This embodiment is substantially the same as the third embodiment, but as shown in FIGS. 23 to 25, a bulge 62 formed by expanding its outer surface side is formed on a base material cover 61 of a base material 60 for forming a valved stent.

The bulge 62 is formed between slit-like open sections 64 in a cylinder 63 of the base material cover 61, and expands to have a crescent sectional shape so that outer surfaces at opposite ends in a circumferential direction match an outer surface of the cylinder 63, and that an outer surface at a center in the circumferential direction protrudes radially outward from the outer surface of the cylinder 63. An expansion height of the bulge 62 from the outer surface of the cylinder 63 is larger on a side closer to a base end in an axial direction of the base material cover 61 so as to form a leaflet 5 having a more expanded shape at a position closer to a front end.

The base material cover 61 has the bulge 62, and thus the leaflet 5 can be formed into a sufficiently expanded shape, and when the leaflet 5 of the valved stent 1 is closed, the leaflets 5 can be brought into contact with each other in a sufficient range and reliably closed. Thin tissue 37 with a sufficient modulus of elasticity is formed on the surface of the bulge 62, and thus the leaflet 5 of the valved stent 1 composed of the tissue 37 is not drawn and damaged, and is easily opened/closed without resisting a flow.

Figure 26:
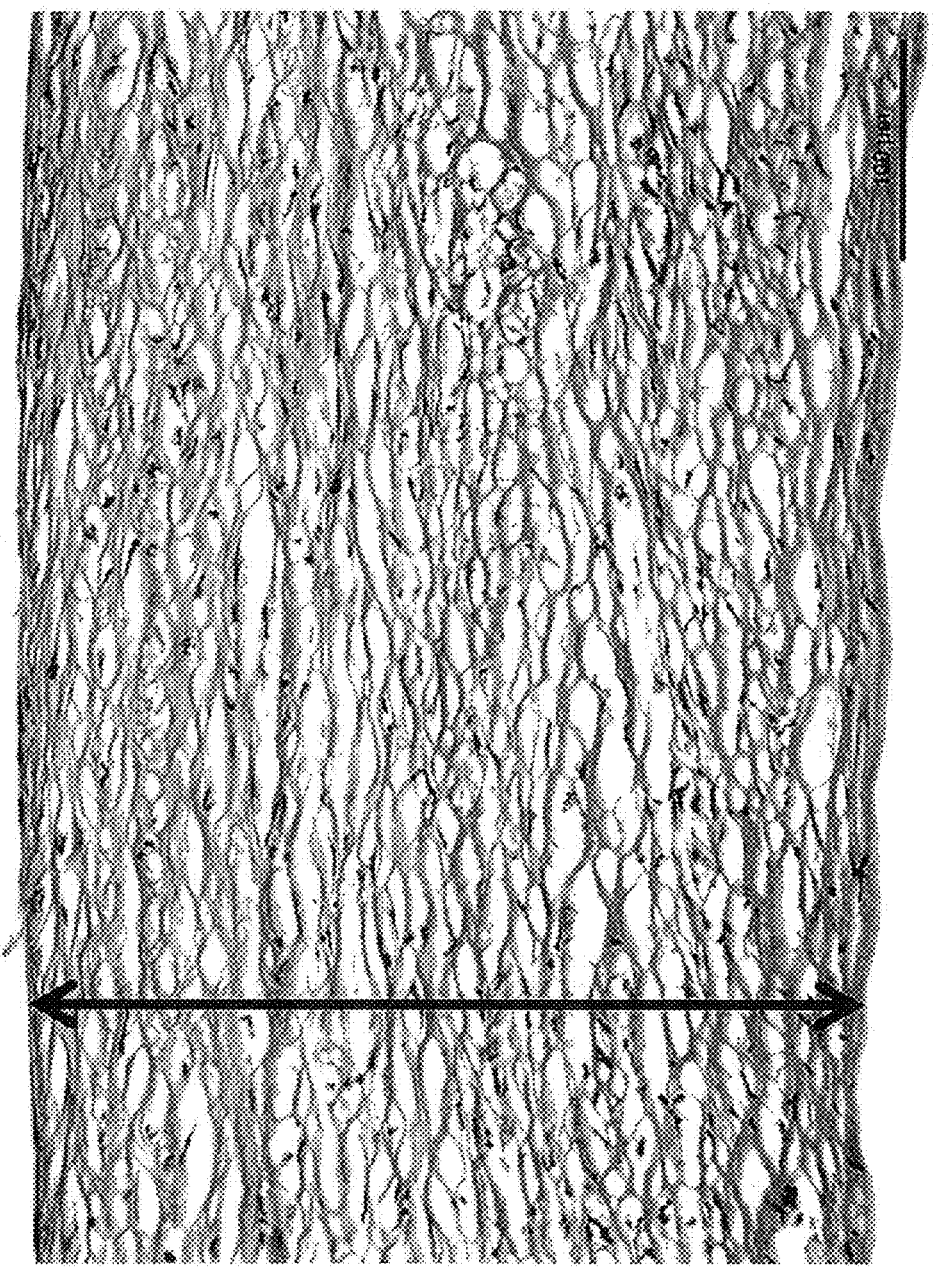
FIG. 26 is a photograph of a section of tissue (expansion height of 0 mm).
Figure 27:
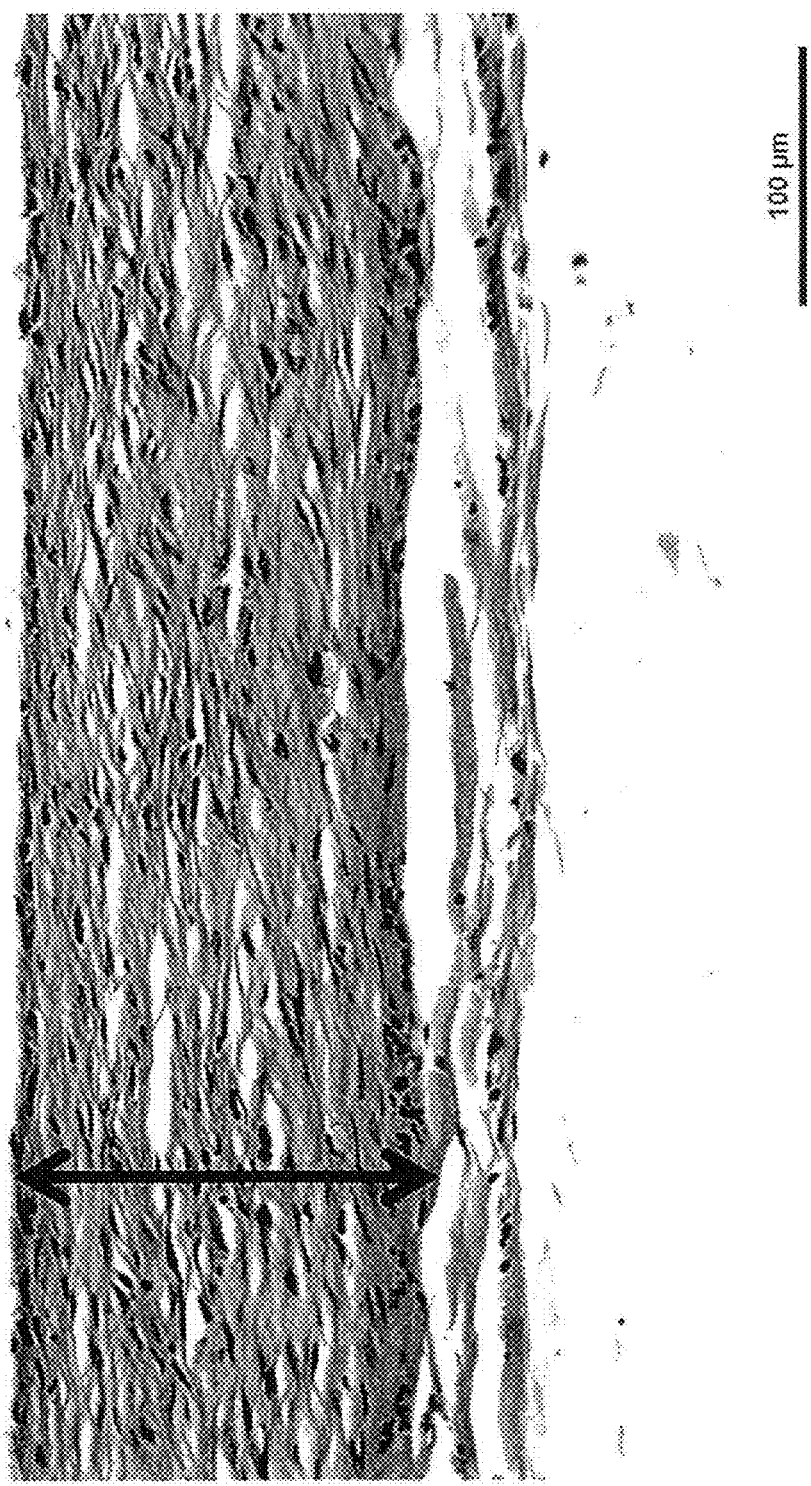
FIG. 27 is a photograph of a section of tissue (expansion height of 2 mm).
Figure 28:
FIG. 28 is a photograph of a section of tissue (expansion height of 3 mm).

Next, an influence of the expansion height of the bulge 62 on the tissue will be described. FIGS. 26 to 28 are photographs of a section of tissue formed on the surface of the bulge 62 which were taken in such a manner that the base material 60 for forming a valved stent having a diameter of 17 mm was embedded under skin of a goat, and after one month passed, tissue formed on the surface of the bulge 62 was delaminated and cut, and a section thereof was photographed. In the drawings, a range indicated by an arrow shows a thickness of the tissue used as the leaflet 5.

FIG. 26 is a photograph of a section of tissue formed on a surface of a cylinder without a bulge, and shows thick non-dense tissue being formed. FIG. 27 is a photograph of a section of tissue formed on a surface of a bulge having an expansion height of 2 mm, and shows thin dense tissue being formed. FIG. 28 is a photograph of a section of tissue formed on a surface of a bulge having an expansion height of 3 mm, and shows thinner dense tissue than the tissue in FIG. 27 being formed.

The thickness of each tissue was measured, and was 356±105 (μm) at an expansion height of 0 mm (FIG. 26), 143±62 (μm) at an expansion height of 2 mm (FIG. 27), and 72±34 (μm) at an expansion height of 3 mm (FIG. 28).

The modulus of elasticity of each tissue was measured, and each of the moduli of elasticity was 2762±589 (kPa) at an expansion height of 0 mm (FIG. 26), 2055±329 (kPa) at an expansion height of 2 mm (FIG. 27), and 1908±162 (kPa) at an expansion height of 3 mm (FIG. 28). These were significantly higher than a modulus of elasticity of 494±169 (kPa) of an aorta of a goat or a modulus of elasticity of 1097±389 (kPa) of a leaflet of a goat.

A method for measuring the modulus of elasticity will now be described. The modulus of elasticity was measured using a precision measuring system manufactured by Axiom Co., Ltd. Specifically, a rectangular sheet-like tissue was secured to a stage with a bore having a diameter of 5 mm at its center, and a cylindrical probe having a diameter of 1 mm was pressed down at its central position of the bore at a speed of 0.1 mm/s until the sample was broken. Further, a moving distance of the probe and a load on the probe during the pressing were continuously measured, and the modulus of elasticity was measured from a relationship between the moving distance of and the load on the probe.

Each time of measurement was finished, the sample was displaced, and the measurement was repeated. A total of five times of measurements were performed, and the modulus of elasticity of each sample was calculated from an average value of the five measurements. This operation was repeated for six evaluation samples, and finally an average was calculated from an average value (n=5) of the six samples, and this value was determined as the "modulus of elasticity."

Also, the modulus of elasticity was calculated using Expressions (1) to (4) below, and an average value of five measurement values was calculated.

$$k = P/\delta \tag{1}$$

$$G = k(1-\nu)/(4r_\theta) \tag{2}$$

$$E = 2G(1+\nu) \tag{3}$$

$$E = k(1-\nu^2)/(2r_\theta) = P(1-\nu^2)/(2\delta r_\theta) \tag{4}$$

Characters in the above expressions represent the following:
ν: Poisson's ratio (calculated as 0.5)
$r_\theta$: probe radius (m)
P: load (g)
δ: amount of entry of probe (m)
k: spring constant
G: modulus of elasticity in shear
E: modulus of elasticity (kPa)

As described above, with higher expansion height of the bulge 62, thinner tissue is formed on the surface of the bulge 62, and in addition, the modulus of elasticity of the tissue is not extremely reduced, and tissue having a sufficient modulus of elasticity can be obtained as compared to the modulus of elasticity of the aorta or the leaflet of the goat. Other configurations are the same as in the third embodiment.

Fifth Embodiment

Figure 29:
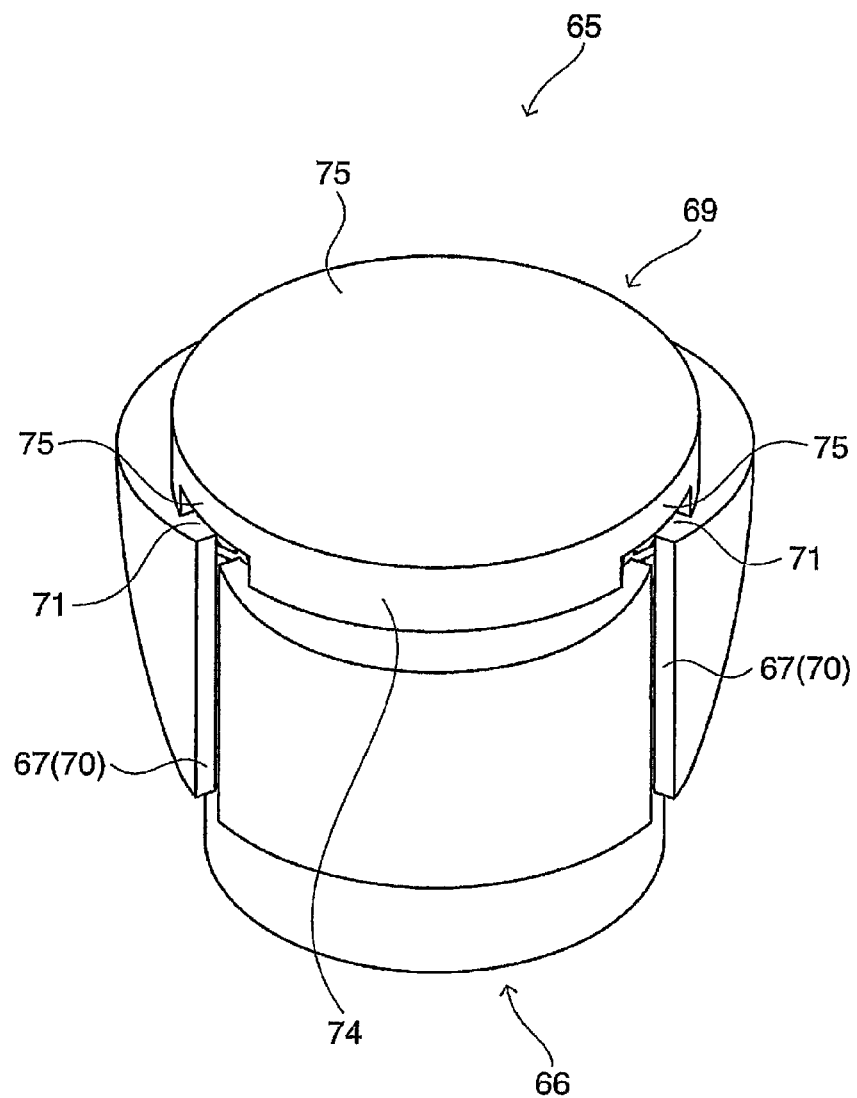
FIG. 29 is a perspective view of a base material for forming a valved stent (fifth embodiment).
Figure 30:
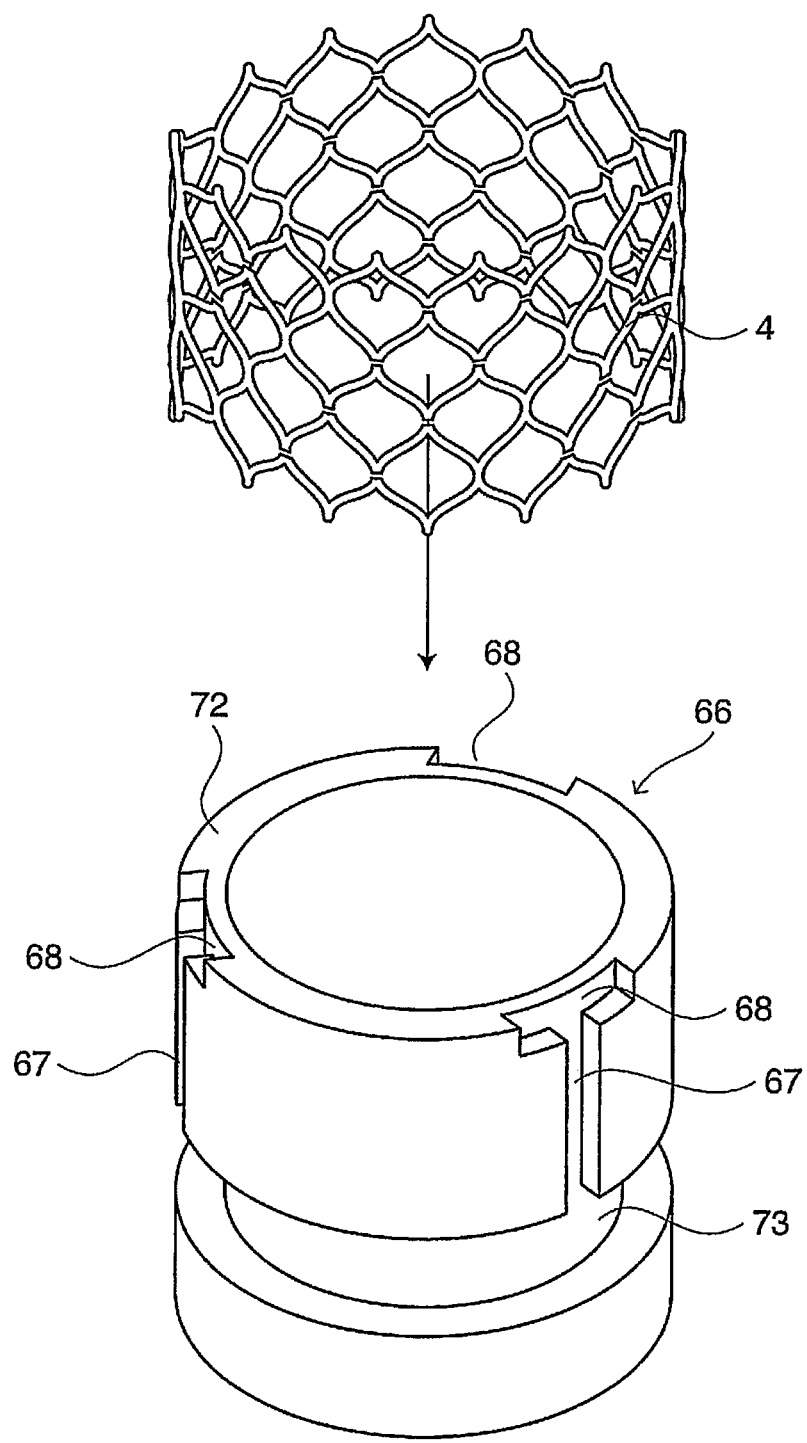
FIG. 30 is a perspective view of a base material body (fifth embodiment).
Figure 31:
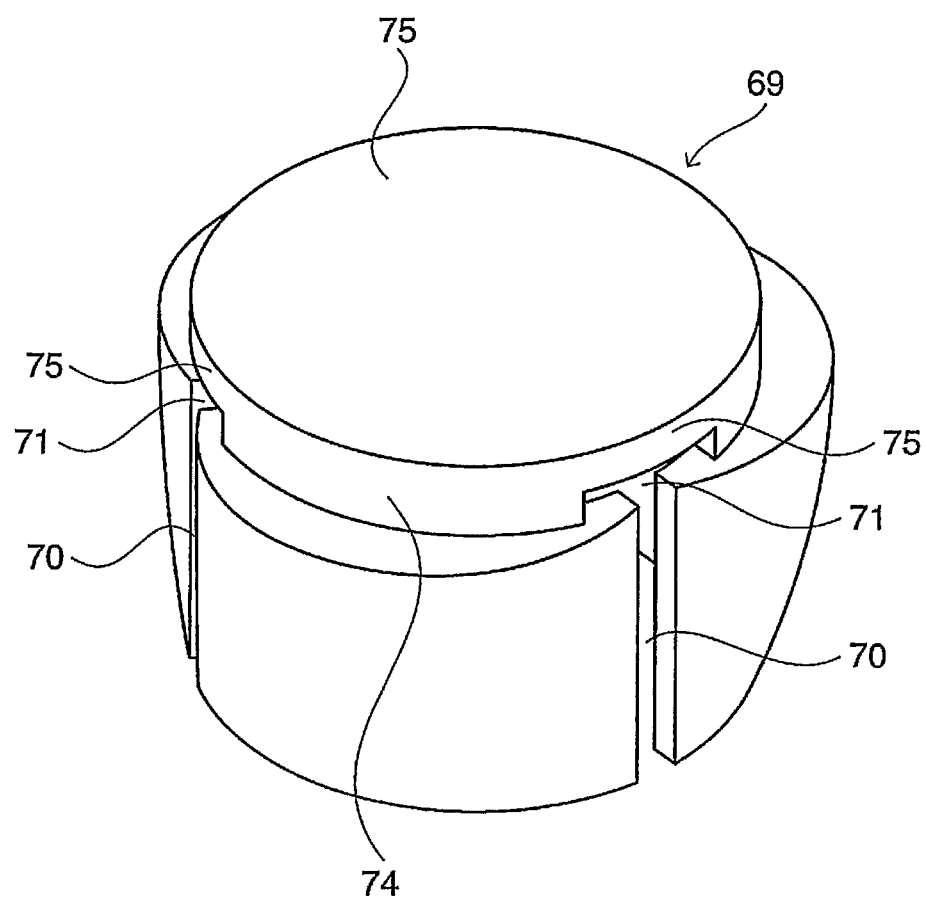
FIG. 31 is a perspective view of a base material cover (fifth embodiment).

This embodiment is substantially the same as the fourth embodiment, but as shown in FIGS. 29 to 31, a lateral groove 68 crossing an entry groove 67 is formed in a base material body 66 of a base material 65 for forming a valved stent, and a lateral open section 71 crossing an open section 70 is formed in a base material cover 69.

The lateral groove 68 has substantially the same groove width and groove depth as the entry groove 67, is shorter than the entry groove 67, and is formed perpendicularly to the entry groove 67 at an end opposite to a peripheral groove 73 in a central axial direction of a cylinder 72 of the base material body 66.

The lateral open section 71 has substantially the same width as the open section 70, is shorter than the open section 70, and is formed perpendicularly to the open section 70 in a region adjacent to a flange 75 at a base end of a cylinder 74 of a base material cover 69.

With the base material cover 69 being placed over the base material body 66, the lateral groove 68 overlaps the lateral open section 71, and connective tissue enters the lateral groove 68 and the lateral open section 71. Thus, a T-shaped reinforcement section is formed at a front end of a contact section 6 formed in the entry groove 67 and the open section 70, and the contact section 6 and a stent body 4 are more firmly integrated. Other configurations are the same as in the fourth embodiment.

REFERENCE SIGNS LIST

1 Valved stent (first to fifth embodiments)
2 Blood vessel
3 Ampulla
4 Stent body
5 Leaflet 6 Contact section
7 Exposed portion
8 Branch blood vessel
10 Leaflet base end
11 Base material for forming a valved stent (first embodiment)
12 Base material body
13 Recess
14 Leaflet forming space
15 Inner cover
16 Outer cover
22 Boundary
23 Taper
24 Cover piece
26 Open section
31 Cover piece
34 Open section
37 Tissue
38 Reverse valved stent (second to fifth embodiments)
39 Base material for forming a valved stent (second embodiment)
40 Base material body
41 Base material cover
42 Entry groove
46 Cover piece
49 Open section
50 Base material for forming a valved stent (third embodiment)
51 Base material cover
52 Open section
53 Base material body
54 Entry groove
60 Base material for forming a valved stent (fourth embodiment)
61 Base material cover
62 Bulge
64 Open section
65 Base material for forming a valved stent (fifth embodiment)
66 Base material body
67 Entry groove
68 Lateral groove
69 Base material cover
70 Open section
71 Lateral open section

The invention claimed is:

1. A base material for forming a valved stent that is capable of receiving a stent body, and that is capable of being placed in an environment with a body tissue material to form tissue on a surface of the base material and form the valved stent including a leaflet protruding radially inward, the base material comprising:
a columnar base material body;
a plurality of recesses formed in an outer peripheral surface of the columnar base material body;
an inner cover that covers the plurality of recesses to form a leaflet forming space for forming the leaflet; and
an outer cover on an outer surface side of the inner cover, the outer cover and the inner cover being capable of receiving the stent body therebetween to prevent tissue from entering between the outer cover and the inner cover.

2. The base material according to claim 1, further comprising:
a first positioning section that circumferentially positions the columnar base material body and the inner cover; and
a second positioning section that circumferentially positions the inner cover and the outer cover.

3. The base material according to claim 1, wherein the tissue to be formed on the surface of the base material is a film.

* * * * *